United States Patent
Bruno et al.

(10) Patent No.: US 6,534,483 B1
(45) Date of Patent: Mar. 18, 2003

(54) PROTECTED ONE-VIAL FORMULATION FOR NUCLEIC ACID MOLECULES, METHODS OF MAKING THE SAME BY IN-LINE MIXING, AND RELATED PRODUCTS AND METHODS

(75) Inventors: Maria Bruno, Caguas, PR (US); Jenna Tagliaferri, Houston, TX (US); Luke Lawson, Spring, TX (US); Mark J. Logan, The Woodlands, TX (US); Russ Mumper, The Woodlands, TX (US)

(73) Assignee: Valentis, Inc., Burlingame, CA (US)

( * ) Notice: Subject to any disclaimer, the term of this patent is extended or adjusted under 35 U.S.C. 154(b) by 0 days.

(21) Appl. No.: 09/371,619

(22) Filed: Aug. 10, 1999

Related U.S. Application Data

(60) Provisional application No. 60/096,572, filed on Aug. 14, 1998.

(51) Int. Cl.[7] .................................................. A61K 31/713
(52) U.S. Cl. ........................... 514/44; 435/6; 435/320.1; 435/458; 435/283.1
(58) Field of Search ........................ 435/6, 320.1, 458; 514/283.1, 44

(56) References Cited

U.S. PATENT DOCUMENTS

| | | | | |
|---|---|---|---|---|
| 4,897,355 A | | 1/1990 | Eppstein et al. .......... | 435/240.2 |
| 5,039,540 A | | 8/1991 | Ecanow ...................... | 426/385 |
| 5,079,018 A | | 1/1992 | Ecanow ...................... | 426/385 |
| 5,300,779 A | * | 4/1994 | Hillman et al. ............ | 250/341 |
| 5,676,954 A | | 10/1997 | Brigham ..................... | 424/450 |
| 5,738,898 A | * | 4/1998 | Smith et al. ................ | 426/614 |
| 5,763,158 A | * | 6/1998 | Bohannon ..................... | 435/4 |
| 5,811,406 A | * | 9/1998 | Szoka, Jr. et al. ............ | 514/44 |
| 6,303,378 B1 | | 10/2001 | Bridenbaugh et al. | |

FOREIGN PATENT DOCUMENTS

| | | |
|---|---|---|
| WO | 93/00807 | 1/1993 |
| WO | 93/09236 | 5/1993 |
| WO | 93/18759 | 9/1993 |
| WO | 93/19768 | 10/1993 |
| WO | 96/21470 | 7/1996 |
| WO | 96/24664 | 8/1996 |
| WO | 96/34109 | 10/1996 |
| WO | 96/39124 | 12/1996 |
| WO | 96/41873 | 12/1996 |
| WO | WO 99/22009 | 5/1999 |
| WO | WO 99/40771 | 8/1999 |

OTHER PUBLICATIONS

W. French Anderson, Human gene therapy, Nature vol. 392, Supp, Apr. 1998.*
Inder M. Verma et al, Gene therapy–promises, problems and prospects, Nature vol. 389, Sep. 1997.*
Bardat A. et al., "Moisture Measurement: A New Method for Monitoring Freeze–drying Cycles", Technology Applications, 1993.
FTS Systems, "Basic Theory of Freeze Drying/Lyophilization", Product Support Information, Bulletin #1, pp. 1–19.
Her LM et al., "Measurement of Glass Transition Temperatures in Freeze Concentrated Solutions of Non–Electrolytes by Electrical Thermal Analysis", Pharmaceutical Research, vol. 11, No. 7 pp. 1023–1029, 1994.
Phase Technologies, Inc., "Lactose 3% wt/wt", D2 Report, pp. 1–9, 1992.
Reiter C., "Significant design changes in laboratory/research freeze dryers", American Laboratory, News Edition, 1991.
Roy M. L. et al., "Process Control in Freeze Drying: Determination of the End Point of Sublimation Drying by an Electronic Moisture Sensor", J. Parenter Sci Technology, vol. 43, No. 2, pp. 60–66, 1989.
Mumper et al., "Protective interactive noncondensing (PINC) polymers for enhanced plasmid distribution and expression in rat skeletal muscle" *Journal of Controlled Release* 52 (1998) 191–203.
ED: Budavari et al.: "The Merk Index, Twelfth Edition", 1996, Merk & Co., Inc., Whitehouse Station, NJ XP002130975 entry 1086, p. 177.
ED: Budavari et al.: "The Merk Index, Twelfth Edition", 1996, Merk & Co., Inc., Whitehouse Station, NJ XP002130975 entry 867, pp. 139–140.
Armstrong, "Use of capacitance manometer gauge in vacuum freeze–drying," *Journal of Parenteral Science and Technology* 34(6):473–483 (1980).
Ausubel et al.(editor), *Current Protocols in Molecular Biology*, John Wiley & Sons (1994) (Table of Contents for vols. 1 & 2).
Bollon and Stauver, "DNA Transformation Efficiency of Various Bacterial and Yeast Host–Vector Systems," *Journal of Clinical Hematology and Oncology* 10(2&3):39–48 (1980).
Botstein et al., "Making Mutations in vitro and Putting Them Back into Yeast," *Miami Winter Symposia—From Gene to Protein: Translation into Biotechnology*, edited by Ahmad et al., Academic Press, 19:265–274 (1982).
Broach, "The Yeast Plasmid 2μ Circle," *Cell* 28:203–204 (1982).

(List continued on next page.)

*Primary Examiner*—James Ketter
(74) *Attorney, Agent, or Firm*—Michael J. Wise; Perkins Coie LLP

(57) ABSTRACT

The present invention, as noted above, relates generally to the incorporation of plasmid into a conventional dosage form, and more particularly to the production of a single-vial, homogenized, plasmid/polymer complex with desirable physical characteristics. Methods of making, storing and using such a complex are also provided and described in detail below. Such products and methods will provide more convenient and cost-effective complexes, which will be protected against chemical degradation and/or physical aggregation of its components and will provide for relative ease of administration. Thus, the present invention provides a more efficient complex for plasmid delivery and a method of incorporation of that plasmid into a conventional dosage form.

39 Claims, 2 Drawing Sheets

OTHER PUBLICATIONS

Broach, "The Yeast Plasmid 2$\mu$ Circle," in *The Molecular Biology of the Yeast Saccharomyces: Life Cycle and Inheritance*, Cold Spring Harbor Laboratory, Cold Spring Harbor, NY, pp. 445–470 (1981).

Capecchi, "High Efficiency Transformation by Direct Microinjection of DNA into Cultured Mammalian Cells," *Cell* 22:479–488 (1980).

Chater et al., "Streptomyces $\phi$C31–Like Phages: Cloning Vectors, Genome Changes and Host Range," in *Sixth International Symposium on Actinomycetes Biology*, Akademiai Kaido, Budapest, Hungary, pp. 45–52 (1986).

Chen and Okayama, "High–Efficiency Transformation of Mammalian Cells by Plasmid DNA," *Molecular and Cellular Biology* 7(8):2745–2752 (1987).

Chu et al., "Electroporation for the efficient transfection of mammalian cells with DNA," *Nucleic Acids Research* 15:1311–1326 (1987).

Curiel et al., "Gene Transfer to Respiratory Epithelial Cells via the Receptor–mediated Endocytosis Pathway," *Am. J. Respir. Cell. Mol. Biol.* 6:247–252 (1992).

Davis et al., "Plasmid DNA is Superior to Viral Vectors for Direct Gene Transfer into Adult Mouse Skeletal Muscle," *Human Gene Therapy* 4:733–740 (1993).

Davis et al., "Direct gene tranfer into skeletal muscle in vivo: Factors affecting efficiency of transfer and stability of expression," *Hum. Gene Ther.* 4:151–159 (1993).

Dowty and Wolff, "Possible mechanisms of DNA uptake in skeletal muscle," in *Gene Therapeutics: Methods and Applications of Direct Gene Transfer*, edited by J.A. Wolff, Birkhauser, Boston, pp. 82–98 (1994).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Galaev et al., "Interaction of Cibacron Blue with polymers: implications for polymer–shielded dye–affinity chromatography of phosphofructokinase from baker's yeast," *Journal of Chromatography A* 684:45–54 (1994).

Gao and Huang, "Cationic liposome–mediated gene transfer," *Gene Therapy* 2:710–722 (1995).

Gold et al., "Translational Initiation in Prokaryotes," *Ann. Rev. Microbiol.* 35:365–403 (1981).

Gryczan, "Ch. 10—Molecular Cloning in *Bacillus subtilis*," in *The Molecular Biology of the Bacilli*, edited by Dubnau, Academic Press, New York, pp. 307–329 (1982).

Izaki, *Jpn. J. Bacteriol.* 33:729–742 (1978).

Jasny, "Insect Viruses Invade Biotechnology," *Science* 238:1653 (1987).

Jennings et al., "Optimization of the hyophilization schedule," *Drug & Cosmetic Industry*, pp. 43–52 (1980).

Jennings, "Residual gas analysis and vacuum freeze drying," *Journal of Parenteral Science and Technology* 34(1):62–69 (1980).

Jennings, "Discussion of primary drying during lyophilization," *Journal of Parenteral Science and Technology* 42:118–121 (1988).

Jennings, "Effect of pressure on the sublimation rate of ice," *Journal of Parenteral Science and Technology* pp. 95–97 (1986).

Jennings, "Thermal–analysis instrumentation for liophylization," *Med. Dev. & Diag. Ind.* 2(11):49–56 (1980).

John et al., "Plasmids as Epidemiologic Markers in Nosocomial Gram–Negative Bacilli: Experience at a University and Review of the Literature," *Rev. Infect. Dis.* 8:693–704 (1986).

Kabanov and Kabanov, "DNA Complexes with Polycations for the Delivery of Genetic Material Into Cells," *Bioconj. Chem.* 6:7–20 (1995).

Kabanov et al., "DNA Interpolyelectroylte Complexes as a Tool for Efficient Cell Transformation," *Biopolymers* 31:1437–1443 (1991yaarerefadfdfadf.

Kendall and Cohen, "Plasmid Transfer in *Streptomyces lividans*: Identification of a kil–kor System Associated with the Transfer Region of PIJ101," *Journal of Bacteriology* 169:4177–4183 (1987).

Leebron et al., "Determination of the vacuum outgassing properties of elastic closures by mass spectrometry," *Journal of Parenteral Science and Technology* 35(3):100–105 (1981).

Livesey et al., "A discussion of the effect of chamber pressure on heat and mass transfer in freeze–drying," *Journal of Parenteral Science and Technology* 41(5):169–171 (1987).

Maniatis, "Ch. 11—Recombinant DNA Procedures in the Study of Eukaryotic Genes," in *Cell Biology: A Comprehensive Treatise, Volume 3, Gene Sequence Expression*, Academic Press, NY, pp. 563–608 (1980).

Miller et al., "An Insect Baculovirus Host–Vector System for High–Level Expression of Foreign Genes," in *Genetic Engineering: Principles and Methods*, edited by Setlow et al., Plenum Press, 8:277–298 (1986).

Miller, "Human Gene Therapy Comes of Age," *Nature* 357:455–460 (1992).

Mulligan, "The Basic Science of Gene Therapy," *Science* 260:926–932 (1993).

Mumper et al., "Polyvinyl Derivatives as Novel Interactive Polymers for Controlled Gene Delivery to Muscle," *Pharmaceutical Research* 13(5):701–709 (1996).

Nail et al., "Methodology for in–process determination of residual water in freeze–dried products," *Develop. Biol. Stand.* 74:137–151 (1991).

Okayama and Berg, "A cDNA Cloning Vector That Permits Expression of cDNA Inserts in Mammalian Cells," *Molecular and Cellular Biology* 3:280–289 (1983).

*Perry's Chemical Engineer's Handbook*, Section 21, p. 57–58, 6$^{th}$ Ed., (1984).

Rubin, "*Drosophila melanogaster* as an Experimental Organism," *Science* 240:1453–1459 (1988).

Sambrook and Maniatis, *Molecular Cloning: A Laboratory Manual, 2$^{nd}$ Edition*, Cold Spring Harbor Press (1989) (Table of Contents for Vol. 1, 2 and 3).

Lindahl et al., "Rate of depurination of native deoxyribonucleic acid," *Biochemistry* 11(19):3610–3618 (1972).

Tarantino et al., "N–Methyl–2–pryyolidone as a Cosolvent: Relationship of Cosolvent Effect of Solute Polarity and the Presence of Proton–Donating Groups on Model Drug Compounds," *Journal of Pharmaceutical Sciences* 83(9):1213–1216 (1994).

Thompson et al., "Evolving instrumentation for freeze–drying," *InTech* pp. 48–49 (1995).

Volker Buhler—BASF Aktiengesellschaft, *Kollidon®: Polyvinylpyrrolidone for the pharmaceutical industry, 2$^{nd}$ edition*, pp. 39–42 (Aug. 1993).

Williams et al., "The effects of cooling rate on solid phase transitions and associated vial breakage occurring in frozen mannitol solutions," *Journal of Parenteral Science and Technology* 40(4):135–141 (1986).

Wolff et al., "Direct Gene Transfer into Mouse Muscle In Vivo," *Science* 247:1465–1468 (1990).

Yang et al., "In Vivo and In Vitro Gene Transfer to Mammalian Somatic Cells by Particle Bombardment," *Proc. Natl. Acad. Sci. USA* 87:9568–9572 (1990).

Yaroslavov et al., "DNA affinity to biological membranes is enhanced due to complexation with hydrophobized polycation," *FEBS Letters* 384:177–180 (1996).

Zia et al., "Cosolvency of Dimethyl Isosorbide for Steroid Solubility," *Pharmaceutical Research* 8:502–504 (1991).

Ausburn et al., Synthetic (Non–Viral) Vector Manufacturing: Control of Mean Particle Size and Distribution Using Static Mixers in a Continuous Process, American Society of Gene Therapy 1$^{st}$ Annual Meeting, May 28–31, 1998.

Ausburn et al., Synthetic (Non–Viral) Vector Manufacturing: Control of Mean Particle Size and Distribution Using Static Mixers in a Continuous Process, American Society of Gene Therapy 1$^{st}$ Annual Meeting, May 28–31, 1998.

* cited by examiner

PROTECTED ONE-VIAL FORMULATION FOR NUCLEIC ACID MOLECULES, METHODS OF MAKING THE SAME BY IN-LINE MIXING, AND RELATED PRODUCTS AND METHODS

RELATED APPLICATIONS

This application claims priority to U.S. Provisional Application No. 60/096,572, entitled, "Protected One-Vial Formulation for Nucleic Acid Molecules, Methods of Making the Same By Inline Mixing, and Related Products and Methods," by Bruno, et al., filed on Aug. 14, 1998. Which is incorporated by reference herein in its entirety including drawings.

INTRODUCTION

The present invention relates to products and methods useful for the production of a single-vial lyophilized nucleic acid/formulating agent complex with favorable physical and dosage characteristics.

BACKGROUND OF THE INVENTION

None of the information provided herein is admitted to be prior art to the present invention, but is provided only to aid the understanding of the reader.

Gene therapy has become a major area of research in rug development. More practical and effective gene delivery methods continue to aid the advancement of the clinical and/or commercial uses of gene therapy, which generally are expected to deliver the product to the targeted cells in sufficient quantities.

In the past, incorporation of nucleic acid into a conventional dosage form has been a challenge due to the chemical degradation or physical aggregation of the nucleic acid prior to administration. The preferred method of administration of a nucleic acid complex is in a liquid form, so past methods have included storing the nucleic acid in a separate vial and combining the necessary components shortly prior to administration. This was a generally effective method, however it was relatively expensive and difficult to prepare and produced a rather unstable product which was somewhat difficult to administer. The stabilization of polynucleotide complexes by adding a cryoprotectant compound and lyophilizing the resulting formulation is described in Szoka et al., International Patent Publication No. WO 96/41873, published Dec. 27, 1996, entitled "Dry Powder Formulations of Polynucleotide Complexes", incorporated herein by reference in its entirety, including any drawings.

In prior attempts to make nucleic acid formulations, the method of mixing has typically been a conventional, slow (but not controlled) mixing of the DNA complex and formulating agent. The result was a non-homogenous complex with particles of relatively large size (approximately 150 nanometers). For ease of administration of the DNA complex, it would be desirable to have a smaller and more uniform particle size. Thus, despite the above, there remains a need for a single-vial homogenized nucleic acid formulation of a relatively small and uniform particle size, especially one protected from degradation and with an increased ability to transfect cells relative to the non-formulated nucleic acid, as well as easier methods of preparation and storage.

SUMMARY OF THE INVENTION.

This invention features compositions and methods for a cost-effective production of isolated, enriched or purified nucleic acids, preferably DNA plasmid, in a conventional dosage form without significant reduction of its biological activity. Thus, the present invention provides a single-vial, homogenized complex created by in-line mixing, where the resulting complex is lyophilized for storage and re-hydrated for administration. The in-line mixing preferably utilizes two tubes which lead into a mixer and which will serve to produce a mixture of a nucleic acid and a formulating agent. The complex in this invention, though formulated in a single vial, maintains favorable physical characteristics and potency. The use of this single vial formulation will result in: (1) reduced manufacturing costs, (2) ease of manufacturing and quality control testing, (3) product stability, and (4) increased doctor/patient compliance and relative ease of administration. These attributes, and the details that follow, provide advantages over the previously used formulations.

Thus, in one aspect, the invention features an in-line mixer containing a confined flowing system of isolated, enriched or purified liquid nucleic acid molecules.

By an "in-line mixer" is meant a device through which liquids to be contacted with one another are passed and which is used for continuous or semibatch operations. The mixer may include tubing and together with the liquid forms a confined flowing system. The volume of liquid in the mixer is limited only by the size and shape of the mixer. The mixers may utilize mechanical agitation, but when mechanical agitation is not used, other methods such as jet mixers, injectors, orifices, mixing nozzles, valves, and pumps may be used. Many in-line mixers are used commercially in chemical and chemical engineering applications, such as in the treatment of petroleum distillates, in vegetable oil refining, in some metal extractions and other applications. Because many types of these mixers are commercially available for use in chemistry and chemical engineering, those skilled in the art could easily design and make other in-line mixers with minor modifications that would still be suitable for treating nucleic acids as described herein.

The in-line mixer preferably is made up of two inlets in a Y-shaped configuration which join at an intersection to form a single outlet. In one embodiment of the invention, the in-line mixer includes a static mixer after the Y-shaped intersection.

By "nucleic acid molecules", it is meant polynucleotides, i.e., a polymer of deoxyribonucleotides (DNA) or ribonucleotides (RNA) which includes naked DNA, a nucleic acid cassette, naked RNA, nucleic acid contained in vectors or viruses, both RNA and DNA including: cDNA, genomic DNA, plasmid DNA or condensed nucleic acid, nucleic acid formulated with cationic lipids, nucleic acid formulated with peptides, antisense molecules, cationic substances, RNA or mRNA. Examples of suitable nucleic acid molecules include those described in Szoka et al., International Application "Dry Powder Formulations of Polynucleotide Complexes", International Patent Publication No. WO 96/41873, published Dec. 27, 1996, and Rolland, et al., International Patent Publication WO 96/21470, published Jul. 18, 1996, entitled, "Formulated Nucleic Acid Compositions and Methods of Administering the Same for Gene Therapy" which are incorporated herein by reference in their entirety, including any drawings. These are only examples and are not meant to be limiting. Additionally the nucleic acid molecules may be one or more plasmids with a eukaryotic promoter that expresses one or more therapeutic molecules. The nucleic acid molecules are, in certain aspects and embodiments, isolated, purified or enriched, as defined below in the Detailed Description at Section I.D.

The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

In a preferred embodiment, the nucleic acid administered is plasmid DNA which includes a "vector". The nucleic acid can be, but is not limited to, a plasmid DNA vector with a eukaryotic promoter which expresses a protein with potential therapeutic action, such as, for example; hGH, VEGF, EPO, IGF-1, TPO, Factor IX, IFN-α, IFN-β, IL-2, IL-12, or the like.

As used herein, the term "plasmid" refers to a construct made up of genetic material (i.e., nucleic acids). It includes genetic elements arranged such that an inserted coding sequence can be transcribed in eukaryotic cells. Thus, the plasmid preferably is an extrachromosomal genetic element consisting of a circular duplex of DNA which can replicate independently of chromosomal DNA. Plasmids are used in gene transfer, as the vehicle by means of which DNA fragments can be introduced into a host organism, and are associated with the transfer of antibiotic resistance.

The term "vector" as used herein refers to a construction comprised of genetic material designed to direct transformation of a targeted cell. A vector contains multiple genetic material, preferably contiguous fragments of DNA or RNA, e.g., DNA derived from a plasmid, cosmid, phasmid or bacteriophage or synthesized by chemical or enzymatic means, positionally and sequentially oriented with other necessary elements such that the nucleic acid can be transcribed and when necessary translated in the transfected cells. The vector can contain one or more unique restriction sites for this purpose, and may be capable of autonomous replication in a defined host or organism such that the cloned sequence is reproduced. The vector may have a linear, circular, or supercoiled configuration and may be complexed with other vectors or other materials for certain purposes. The components of a vector can include but are not limited to a DNA molecule incorporating: (1) a sequence encoding a therapeutic or desired product; and (2) regulatory elements for transcription, translation, RNA stability and replication.

In the present invention the preferred vector comprises the following elements linked sequentially at an appropriate distance to allow functional expression: a promoter, a 5' mRNA leader sequence, a translation initiation site, a nucleic acid cassette containing the sequence to be expressed, a 3' mRNA untranslated region, and a polyadenylation signal sequence. As used herein the term "expression vector" refers to a DNA vector that contains all of the information necessary to produce a recombinant protein in a heterologous cell.

In addition, the term "vector" as used herein can also include viral vectors, although non-viral vectors are preferred. A "viral vector" in this sense is one that is physically incorporated in a viral particle by the inclusion of a portion of a viral genome within the vector, e.g., a packaging signal, and is not merely DNA or a located gene taken from a portion of a viral nucleic acid. Thus, while a portion of a viral genome can be present in a vector of the present invention, that portion does not cause incorporation of the vector into a viral particle and thus is unable to produce an infective viral particle.

A vector as used herein can also include DNA sequence elements which enable extra-chromosomal (episbmal) replication of the DNA. Vectors capable of episomal replication are maintained as extra-chromosomal molecules and can replicate. These vectors are not eliminated by simple degradation but continue to be copied. These elements may be derived from a viral or mammalian genome. These provide prolonged or "persistent" expression as described below.

The term "persistent expression" as used herein refers to introduction of genes into the cell together with genetic elements which enable episomal (i.e., extrachromosomal) replication. This can lead to apparently stable transformation of the cell without the integration of the novel genetic material into the chromosome of the host cell.

"Stable expression" as used herein relates to the integration of genetic material into chromosomes of the targeted cell where it becomes a permanent component of the genetic material in that cell. Gene expression after stable integration can permanently alter the characteristics of the cell and its progeny arising by replication leading to stable transformation.

The vector can be used to provide expression of a nucleic acid sequence in tissue. In the present invention this expression preferably is enhanced by providing stability to an mRNA transcript from the nucleic acid sequence and/or secretion of the therapeutic protein. Expression includes the efficient transcription of an inserted gene or nucleic acid sequence within the vector. Expression products may be proteins including but not: limited to pure protein (polypeptide), glycoprotein, lipoprotein, phosphoprotein, or nucleoprotein. Expression products may also be RNA. The nucleic acid sequence is contained in a nucleic acid cassette. Expression of the nucleic acid can be continuous or controlled by endogenous or exogenous stimuli.

The term "control" or "controlled" as used herein relates to the expression of gene products (protein or RNA) at sufficiently high levels such that a therapeutic effect is obtained. Levels that are sufficient for therapeutic effect are lower than the toxic levels. Levels of expression for therapeutic effect within selected tissues corresponds to reproducible kinetics of uptake, elimination from cell, post-translational processing, and levels of gene expression, and, in certain instances, regulated expression in response to certain endogenous or exogenous stimuli (e.g., hormones, drugs).

The term "nucleic acid cassette" as used herein refers to the genetic material of interest which codes for a protein or RNA. The nucleic acid cassette is positionally and sequentially oriented within the vector such that the nucleic acid in the cassette can be transcribed into RNA, and when necessary, translated into a protein in the transformed tissue or cell. Preferably, the cassette has 3' and 5' ends adapted for ready insertion into a vector, e.g., it has restriction endonuclease sites at each end.

The term "tissue" as used herein refers to a collection of cells specialized to perform a particular function or can include a single cell. The cells may be of the same type or of different types.

In preferred embodiments, the nucleic acid contains a coding region transcriptionally linked to a transcriptional control sequence.

In this context, "transcriptionally linked" means that in a system suitable for transcription, transcription will initiate under the direction of the control sequence(s) and proceed through sequences which are transcriptionally linked with that control sequence(s). Preferably no mutation is created in the resulting transcript, which would alter the resulting translation product.

The term "coding region" or "coding sequence" refers to a nucleic acid sequence which encodes a particular gene product for which expression is desired, according to the normal base pairing and codon usage relationships. Thus, the coding sequence must be placed in such relationship to transcriptional control sequences (possibly including control elements and translational initiation and termination codons) that a proper length transcript will be produced and will result in translation in the appropriate reading frame to produce a functional desired product.

The term "transcriptional control sequence" refers to sequences which control the rate of transcription of a transcriptionally linked coding region. Thus, the term can include elements such as promoters, operators, and enhancers. For a particular transcription unit, the transcriptional control sequences will include at least a promoter sequence.

The plasmid, in preferred embodiments, may also contain a growth hormone 3' untranslated region, preferably from a human growth hormone gene.

A "growth hormone 3' untranslated region" is a sequence located downstream (i.e., 3') of the region encoding material polypeptide and including at least part of the sequence of the natural 3' UTR/poly(a) signal from a growth hormone gene, preferably the human growth hormone gene. This region is generally transcribed but not translated. For expression in eukaryotic cells it is generally preferable to include sequence which signals the addition of a poly-A tail. As with other synthetic genetic elements a synthetic 3' UTR/poly(A) signal has a sequence which differs from naturally-occurring UTR elements. The sequence may be modified, for example by the deletion of ALU repeat sequences. Deletion of such ALU repeat sequences acts to reduce the possibility of homologous recombination between the expression cassette and genomic material in a transfected cell.

The plasmid preferably includes a promoter, a TATA box, a Cap site and a first intron and intron/exon boundary in appropriate relationship for expression of the coding sequence. The plasmid may also include a 5' mRNA leader sequence inserted between the promoter and the coding sequence and/or an intron/5' UTR from a chicken skeletal α-actin gene. Also, the plasmid may have a nucleotide sequence which is the same as the nucleotide sequence of plasmid any of the plasmids described herein.

The plasmid may also include: (a) a first transcription unit containing a first transcriptional control sequence transcriptionally linked with a first 5'-untranslated region, a first intron, a first coding sequence, and a first 3'-untranslated region/poly(A) signal, wherein the first intron is between the control sequence and the first coding sequence; and (b) a second transcription unit containing a second transcriptional control sequence transcriptionally linked with a second 5'-untranslated region, a second intron, a second coding sequence, and a second 3'-untranslated region/poly(A) signal, wherein the second intron is between the control sequence and the second coding sequence.

Additionally, the in-line mixer may contain one or more other liquids, at least one of which is a formulating agent. The formulating agent preferably is a lipid, a peptide, a polymer or a small molecule such as europium. In one embodiment the formulating agent is also a protective, interactive, non-condensing compound.

In a preferred embodiment formulating agents are non-condensing polymers, oils and surfactants. These may be suitable for use as compounds which prolong the localized bioavailability of a nucleic acid: polyvinylpyrrolidones; polyvinylalcohols; propylene glycols; polyethylene glycols; polyvinylacetates; poloxamers (Pluronics) (block copolymers of propylene oxide and ethylene oxide, relative amounts of the two subunits may vary in different poloxamers); poloxamines (Tetronics); ethylene vinyl acetates; celluloses, including salts of carboxymethylcelluloses, methylcelluloses, hydroxypropylcellulose, hydroxypropylmethylcelluloses; salts of hyaluronates; salts of alginates; heteropolysaccharides (pectins); phosphatidylcholines (lecithins); miglyols; polylactic acid; polyhydroxybutyric acid. More preferably some of these compounds may be used as, and are considered protective, interactive, non-condensing compounds (PINC) and others as sustained release compounds, while some may be used in either manner under the respectively appropriate conditions.

By "prolonging the localized bioavailability of a nucleic acid" is meant that a nucleic acid administered to an organism in a composition comprising a formulating agent will be available for uptake by cells for a longer period of time than if administered in a composition without such a compound, for example when administered in a saline solution. This increased availability of nucleic acid to cells could occur, for example, due to increased duration of contact between the composition containing the nucleic acid and a cell or due to protection of the nucleic acid from attack by nucleases. The compounds which prolong the localized bioavailability of a nucleic acid are suitable for internal administration.

By "suitable for internal administration" is meant that the compounds are suitable to be administered within the tissue of an organism, for example within a muscle or within a joint space, epidermally, intradermally or subcutaneously. Properties making a compound suitable for internal administration can include, for example, the absence of a high level of toxicity to the organism as a whole.

In another embodiment cationic condensing agents such as cationic lipids, peptides, or lipopeptides, or for example, dextrans, chitosans, dendrimers, polyethyleneimine (PEI), or polylysine, may associate with the nucleic acid molecule and may facilitate transfection.

The PINC enhances the delivery of the nucleic acid molecule to mammalian cells in vivo, and preferably the nucleic acid molecule includes a coding sequence for a gene product to be expressed in the cell. In many cases, the relevant gene product is a polypeptide or protein. Preferably the PINC is used under conditions so that the PINC does not form a gel, or so that no gel form is present at the time of administration at about 30–40° C. Thus, in these compositions, the PINC is present at a concentration of 30% (w/v) or less. In certain preferred embodiments, the PINC concentration is still less, for example, 20% or less, 10% or less, 5% or less, or 1% or. less. Thus, these compositions differ in compound concentration and functional effect from uses of these or similar compounds in which the compounds are used at higher concentrations, for example in the ethylene glycol mediated transfection of plant protoplasts, or the formation of gels for drug or nucleic acid delivery. In general, the PINCs are not in gel form in the conditions in which they are used as PINCs, though certain of the compounds may form gels under some conditions.

In connection with the protective, interactive, non-condensing compounds, the term "non-condensing" means that an associated nucleic acid is not condensed or collapsed by the interaction with the PINC at the concentrations used in the compositions. Thus, the PINCs differ in type and/or concentration from such condensing polymers. Examples of commonly used condensing polymers include polylysine, and cascade polymers (spherical polycations).

The term "protects" or "protective" or "protected" as used herein refers to an effect of the interaction between such a compound and a nucleic acid such that the rate of degradation of the nucleic acid is decreased in a particular environment, thereby prolonging the localized bioavailability of the nucleic acid molecule. Such degradation may be due to a variety of different factors, which specifically include the enzymatic action of a nuclease. The protective action may be provided in different ways, for example, by exclusion of the nuclease molecules or by exclusion of water.

The term "interactive" as used herein refers to the interaction between PINC's and nucleic acid molecules and/or cell wall components. Preferably, PINC polymers are capable of directly interacting with moieties of nucleic acid molecules and/or cell wall components. These interactions can facilitate transfection by, for example, helping associate the nucleic acid molecule-PINC complex closely with the cell wall as a result of biochemical interactions between the PINC and the cell wall and thereby mediate transfection. These interactions may also provide protection from nucleases by closely associating with the nucleic acid molecule.

Also in connection with such compounds and an associated nucleic acid molecule, the term "enhances the delivery" means that at least in conditions such that the amounts of PINC and nucleic acid is optimized, a greater biological effect is obtained than with the delivery of nucleic acid in saline. Thus, in cases where the expression of a gene product encoded by the nucleic acid is desired, the level of expression obtained with the PINC:nucleic acid composition is greater than the expression obtained with the same quantity of nucleic acid in saline for delivery by a method appropriate for the particular PINC/coding sequence combination.

In preferred embodiments of the above compositions, the PINC is polyvinyl pyrrolidone (PVP), polyvinyl alcohol (PVA), a PVP-PVA co-polymer, N-methyl-2-pyrrolidone (NM2P), ethylene glycol, or propylene glycol. In compositions in which a Poloxamer (Pluronics) is used, the nucleic acid is preferably not a viral vector, i.e., the nucleic acid is a non-viral vector.

In other preferred embodiments, the PINC is bound with a targeting ligand. Such targeting ligands can be of a variety of different types, including but not limited to galactosyl residues, fucosal residues, mannosyl residues, carntitine derivatives, monoclonal antibodies, polyclonal antibodies, peptide ligands, and DNA-binding proteins. The targeting ligands may bind with receptors on cells such as antigen-presenting cells, hepatocytes, myocytes, epithelial cells, endothelial cells, and cancer cells.

In connection with the association of a targeting ligand and a PINC, the term "bound with" means that the parts have an interaction with each other such that the physical association is thermodynamically favored, representing at least a local minimum in the free energy function for that association. Such interaction may involve covalent binding, or non-covalent interactions such as ionic, hydrogen bonding, van der Waals interactions, hydrophobic interactions, and combinations of such interactions.

While the targeting ligand may be of various types, in one embodiment the ligand is an antibody. Both monoclonal antibodies and polyclonal antibodies may be utilized.

The nucleic acid may also be present in various forms. Preferably the nucleic acid is not associated with a compounds(s) which alter the physical form, however, in other embodiments the nucleic acid is condensed (such as with a condensing polymer), formulated with cationic lipids, formulated with peptides, or formulated with cationic polymers.

In preferred embodiments, the protective, interactive non-condensing compound is polyvinyl pyrrolidone, and/or the plasmid is in a solution having between 0.5% and 50% PVP, more preferably about 5% PVP. The DNA preferably is at least about 80% supercoiled, more preferably at least about 90% supercoiled, and most preferably at least about 95% supercoiled.

The formulating agent may also protect the nucleic acid against freezing and may increase transfection rates. The effectiveness of the formulating agent in these two capacities may be seen for example in a comparison of gel electrophoresis results, run after thawing the solutions, of both the nucleic acid alone and with the formulating agent. The resulting gel of the nucleic acid with the formulating agent shows a much higher percentage of supercoiled plasmid. This higher percentage of supercoiled plasmid will therefore result in a higher transfection rate.

The term "formulating agent" as used herein refers to an agent that forms a complex with the nucleic acid. This molecular complex is associated with nucleic acid molecule in either a covalent or a non-covalent manner. The formulating agent should be capable of transporting nucleic acid molecules in a stable state and of releasing the bound nucleic acid molecules into the cellular interior. DNA extraction methods, methods of immunofluorescence, or well known reporter gene methods such as for example CAT, or LacZ containing plasmids, could be used in order to determine the transfection efficiency. The formulating agent should also be capable of being associated with nucleic acid molecules and lyophilized or freeze dried and rehydrated prior to delivery.

In addition, the formulating agent may prevent lysosomal degradation of the nucleic acid molecules by endosomal lysis. Furthermore, the formulating agent may allow for efficient transport of the nucleic acid molecule through the cytoplasm of the cell to the nuclear membrane and into the nucleus and provide protection.

In preferred embodiments, the formulating agent enhances the duration and/or intensity of expression of the desired gene.

By "duration" is meant the amount of time a desired gene is expressed as measured, for example in months, weeks, days, hours, minutes and/or seconds.

By ""intensity" is meant the rate at which a desired gene is expressed, for example mass or volume divided by time.

By "expression" is meant production of the encoded product, preferably by transcription and translation of the desired gene or nucleic acid sequence.

By "desired gene" is meant to refer to any gene or nucleic acid sequence encoding a product desired by the individual using the formulated nucleic acid complex. Examples of desired genes include CAT, and therapeutic agents (capable of at least partially reducing or preventing one or more symptoms of a disease) such as IL-2 and all other cytokines, as well as all intracelullar proteins (e.g., thymadine kinase).

The term "cytokines" is meant to refer to the conventionally recognized group of immunogenic proteins such as IL-2, IL-3, IL-4, IL-6, IL-7, IL-8, IL-12, IL-18, TNF-α, INF-α, IFN-α and IFN-γ.

The formulating agent is preferably selected from the group consisting of: one or more polyvinyl pyrrolidones, one or more cationic lipids, one or more cationic lipids with neutral co-lipids, one or more liposomes, one or more peptides, and one or more lipopeptides.

Preferably the cationic lipid is DOTMA and the neutral co-lipid is cholesterol (chol). DOTMA is 1,2-di-O-octadecenyl-3-trimethylammonium propane, which is described and discussed in Eppstein et al., U.S. Pat. No. 4,897,355, issued Jan. 20, 1990, which is incorporated herein by reference. However, other lipids and lipid combinations may be used in other embodiments. A variety of such lipids are described in Gao & Huang, 1995, *Gene Therapy* 2:710–722, which is hereby incorporated by reference. Other cationic lipid delivery technology is described in Brigham, U.S. Pat. No. 5,676,954, issued Oct. 14, 1997, entitled "Method of In Vivo Delivery of Functioning Foreign Genes" 216/012), incorporated herein by reference in its entirety, including any drawings.

As the charge ratio of the cationic lipid and the DNA is also a significant factor, in preferred embodiments the DNA and the cationic lipid are present in such amounts that the negative to positive charge ratio is between 1:0.1 and 1:10, preferably between 1:0.3 and 1:6, more preferably about 1:3. While preferable, it is not necessary that the ratio be 1:3. Thus, preferably the charge ratio for the compositions is between about 1:0.1 and 1:10, more preferably between about 1:0.3 and 1:6.

The term "cationic lipid" refers to a lipid which has a net positive charge at physiological pH, and preferably carries no negative charges at such pH. An example of such a lipid is DOTMA. Similarly, "neutral co-lipid" refers to a lipid which has is usually uncharged at physiological pH. An example of such a lipid is cholesterol.

Thus, "negative to positive charge ratio" for the DNA and cationic lipid refers to the ratio between the net negative charges on the DNA compared to the net positive charges on the cationic lipid.

As the form of the DNA affects the expression efficiency, the DNA preferably is at least about 80% supercoiled, more preferably at least 90% supercoiled, and most preferably at least 95% supercoiled. The composition preferably includes an isotonic carbohydrate solution, such as an isotonic carbohydrate solution that consists essentially of about 10% lactose. In preferred embodiments, the composition the cationic lipid and the neutral co-lipid are prepared as a liposome having an extrusion size of between 200 and 900 nanometers, more preferably about 800 nanometers. Preferably the liposomes are prepared to have an average diameter of between about and 800 nm, more preferably between about 50 and 400 nm, still more preferably between about 75 and 200 nm, and most preferably about 100 nm. Microfluidization is the preferred method of preparation of the liposomes.

In a second aspect, the invention features a method of making an in-line mixer containing nucleic acid molecules as described above. The method involves the step of adding the nucleic acid molecules to the in-line mixer.

The angle between the two inlets preferably is between 45 and 300 degrees, more preferably between 90 and 240 degrees, and most preferably is between 120 and 180 degrees.

In a third aspect, the invention features a method of using an in-line mixer, involving the step of mixing the nucleic acid molecules with one or more other liquids (including emulsions, colloidal suspensions and other solutions) in the in-line mixer preferably where the liquids are continuously mixed. As the liquids are mixed, they preferably are being added to the Y-shaped configuration via a pump, adding the liquids in a continuous, syringe-like manner. The liquids may be added at a certain Reynolds number, preferably greater than 373, more preferably greater than 560, most preferably greater than 746, for optimal prevention of aggregation of the formulation. Non-Newtonian flow (Reynolds numbers greater than 1,000 with turbulence created in the mixing) may be possible.

By "Reynolds number" it is meant the quotient of the inertial forces in the apparatus divided by the viscous forces in the apparatus.

In a preferred embodiment, the liquids may be combined under conditions that produce a substantially homogenous mixture with particles of a preferred uniform size preferably less than or equal to 100 nm, more preferably less than or equal to 75 nm, most preferably less than or equal to 50 nm.

By "uniform size" it is meant that most of the particles in the complex are approximately the same size and are less than the specified value. To be of uniform size, the particles do not have to be the identical size, but are uniformly smaller than the expected size. In another embodiment, the liquid of nucleic acid molecules may be combined with one, two, three or more other liquids.

In a fourth aspect, the invention features a co-lyophilized complex produced by the co-lyophilization of a nucleic acid molecule in a vector with a formulating agent that protects the nucleic acid molecule against freezing and increases transfection rates.

By "co-lyophilized" it is meant the process by which the mixture of the two or more liquids is freeze-dried to protect against the instability of the nucleic acid in solution. Dehydration preferably take place while the product is in a frozen state and under a vacuum. The basic theory, equipment and methodology relting to lyopholiztion of other materials is well known and those skilled in the art therefore could readily select the appropriate parameters for effective lyophilization. See, FTS Systems, *Basic Theory of Freeze Drying/Lyophilization*, Product Support Information, Bulletin #1:1–19; Nail et al., *Develop. Biol. Standard.*, Vol. 74, pp. 137–151 (1991); Jennings, et al. *D&CI*, pp 43–52 (1980); Reiter, *American Laboratory*, "Significant Design Changes in Laboratory/Research Freeze Dryers", (1991); Thompson et al., *InTech*, "Evolving Instrumentation for Freeze-Drying", (1995); Jennings, *Journal of Parenteral Science and Technology*, Vol. 42:118–121 (1988); Jennings, *MD&DI*, pp 49–56 (1980); Livesey et al., *Journal of Parenteral Science & Technology,* Vol. 41, No. 5;169–171 (1987); Jennings, *Journal of Parenteral Science & Technology*, pp. 95–97 (1986); Leebron et al., *Journal of Parenteral Science & Technology,* Vol. 35, No. 3:100–105 (1981); Williams et al., *Journal of Parenteral Science & Technology*, Vol. 40, No. 4: 135–141 (1986); Roy et al., Research Article, Vol. 43, No. 2:60–66 (1989); Armstrong, *Journal of Parenteral Drug Association*, Vol. 34, No. 6: 473–483 (1980); Jennings, *Journal of the Parental Drug Association*, Vol. 34, No. 1:62–69 (1980) all of which are incorporated herein by reference in their entirety, including any drawings In a preferred embodiment, the formulating agent may be a protective, interactive, non-condensing compound. In especially preferred embodiments the formulating agent may be pre-neutralized polyvinyl pyrrolidone, preferably in a concentration of at least 2.5% or a molecular weight of at least 80 kDa. The formulating agent may also be polyvinyl alcohol present in a weight to weight ratio with the formulating agent of about 1 to 17. In a preferred embodiment the complex will be present in a solution having a pH of preferably 3.5 to 9.0, more preferably 6.5 to 8.0 in order to maximize nucleic acid expression.

In other preferred embodiments, the complex may also include an antimicrobial agent, an anti-oxidant, a buffer, or a cryoprotectant.

By "antimicrobial agent" it is meant any chemical or compound which is capable of destroying or inhibiting the growth of microorganisms. In a preferred embodiment, the antimicrobial agent may be Benzalkonium chloride, Benzyl alcohol, Chlorocresol, Phenylmercuric nitrate, oracetate.

By "anti-oxidant" it is meant a chemical compound or substance that inhibits oxidation. In a preferred embodiment, the anti-oxidant may be Ascorbic acid, Butylhydroxyanisole (BHA), Cysteine, Sodium bisulfate, or Glutathione.

By a "buffer" it is meant a substance that minimizes change in the pH of a solution when an acid or base is added to the solution. In a preferred embodiment, the buffer may be Acetic acid and salt, Succinic acid and borax, Formate and HCl, or Na-citrate buffer.

By "cryoprotectant" it is meant any chemical or compound that will serve to protect a substance during freezing. In a preferred embodiment, the cryoprotectant may be lactose, sucrose, mannitol, trehalose, or polyvinyl pyrrolidone.

In a fifth aspect the invention features the making of a co-lyophilized complex preferably made by combining a liquid of nucleic acid molecules and a liquid formulating agent. Preferably the two liquids are passed through an in-line mixer and continuously mixed. The liquids may be added at a certain Reynolds number, preferably greater than 373, more preferably greater than 560, most preferably greater than 746, for optimal prevention of aggregation of the formulation. In a preferred embodiment, the liquids may be combined under conditions that produce a substantially homogenous mixture with particles of a preferred uniform size preferably less than or equal to 100 nm, more preferably less than or equal to nm, most preferably less than or equal to 50 nm. In another embodiment, the liquid of nucleic acid molecules may be combined with one, two, three or more other liquids.

In a sixth aspect, the invention features a method of using the complex resulting from the in-line mixing, by re-hydration.

By "re-hydration" it is meant to cause the complex to take up fluid, preferably a pharmaceutically acceptable solution such as isotonic saline, buffer or other solution.

In a seventh aspect, the invention features a method of using the complex in the treatment or prevention of a disorder by administration of the complex, in any of the above forms, to a patient in need of such treatment.

By "administration" it is meant the route of introduction of a vector or carrier of DNA into the body. Administration may be intravenous, intramuscular, topical, oral,.or by gene gun or hypospray instrumentation. It can be directly to a target tissue or through systemic delivery. Administration will include a variety of methods, such as direct gene transfer into skin tissue by liposomes, proteoliposomes, calcium phosphate-coprecipitated DNA, DNA coupled to macromolecular complexes, DNA transporters, DNA coded to microprojectiles, coded plasmids, direct microinjection, as well as skin grafts. Direct gene transfer of vectors can be administered by direct microinjection, needle-free injection (see, Barry et al., "Needle-Free Injection of Formulated Nucleic Acid Molecules", U.S. Patent Application, Ser. No. 60/069,754, filed Dec. 6, 1997, incorporated herein by reference in its entirety, including any drawings), sonoporation, electroporation (see, MaClaughlin et al., "Formulations for Electroporation", U.S. Patent Application, Ser. No. 60/088,691, filed, Jun. 8, 1998, incorporated herein by reference in its entirety, including any drawings), liposomes, proteoliposomes, calcium phosphate-coprecipitation, skin grafts, retroviral vectors, DNA coupled to macromolecular complexes, DNA transporters and microprojectiles. Routes of administration include intramuscular, aerosol, oral, topical, systemic, ocular, intraperitoneal and/or intrathecal. See, e.g., Woo, et al, International Application No. PCT/US93/02725, filed Mar. 19, 1993, International Publication No. WO 93/18759, published Sep. 30, 1993, entitled "A DNA Transporter System and Method of Use" hereby incorporated by reference in its entirety, including any drawings and the section on administrative in the detailed description section below.

By "treat" it is meant administration of the nucleic acid as described herein so as to deliver a desired nucleic acid to a cell or tissue for the purposes of expression of the nucleic acid by the cell or tissue. Cell or tissue types of interest may include, but are not limited to: liver, muscle, lung, endothelium, joints, skin, bone, tumors and blood.

By "prevent" it is meant to stop or hinder the disorder from occurring by advance action, the delivery of the nucleic acid to the cell, to inhibit the cell from completing the action it would undergo to express such disorder.

In preferred embodiments, the method involves providing a therapeutically effective amount of the complex.

A "therapeutically effective amount" of a composition is an amount which is sufficient to cause at least temporary relief or improvement in a symptom or indication of a disease or condition. Thus, the amount is also sufficient to cause a pharmacological effect. The amount of the composition need not cause permanent improvement or improvement of all symptoms or indications. A therapeutically effective amount of a cancer therapeutic would be one that reduces overall tumor burden in the case of metastatic disease (i.e., the number of metastases or their size) or one that reduces the mass of the tumor in localized cancers.

The disorder being treated may be localized or systemic disease or condition

A "localized" disease or condition refers to those in which there is specific nerve or muscle damage or atrophy to a defined and limited area of the body. A specific example is disuse atrophy.

A "systemic" disease or condition refers to those which relate to the entire organism, or is widely distributed at a number of locations within the body. Examples include growth disorders, neuropathies, and muscular dystrophy.

In an eighth aspect, the invention features a method of delivering the complex by administration, in any of the above forms, to an organism, preferably an animal.

By "delivery" or "delivering" is meant transportation of nucleic acid molecules to desired cells or any cells. The nucleic acid molecules may be delivered to multiple cell lines, including the desired target. Delivery results in the nucleic acid molecules coming in contact with the cell surface, cell membrane, cell endosome, within the cell membrane, nucleus or within the nucleus, or any other desired area of the cell from which transfection can occur within a variety of cell lines which can include but are not limited to; tumor cells, epithelial cells, Langerhan cells, Langhans' cells, littoral cells, keratinocytes, dendritic cells, macrophage cells, kupffer cells, muscle cells, lymphocytes and lymph nodes.

Preferably, the vector comes into contact with the preferred target cell after administration. Administration as noted above, may involve needle injection into cells, tissues, fluid spaces, or blood vessels, electroporation, transfection, hypospray,. iontophoresis, particle bombardment, or transplantation of cells genetically modified ex vivo. Examples of administration include intravenous, intramuscular, aerosol, oral, topical, systemic, ocular, intraperitoneal and/or intrathecal.

The preferred means for administration of vectors described above involves the use of formulations for delivery to the target cell in which the vector is associated with elements such as lipids, proteins, carbohydrates, synthetic organic compounds, or in-organic compounds which enhance the entry of the vector into the nucleus of the target cell where gene expression may occur. A particular example is polyvinyl pyrrolidone(PVP).

The term "formulation" as used herein refers to non-genetic material combined with the vector in a solution, suspension, or colloid which enhances the delivery of the vector to a tissue, uptake by cells within the tissue, intracellular trafficking through the membrane, endosome or cytoplasm into the nucleus, the stability of the vector in extracellular or intracellular compartments, and/or expression of genetic material by the cell.

In a preferred embodiment of the present invention the vector and formulation comprises a nanoparticle which is administered as a suspension or colloid. The formulation can include lipids, proteins, carbohydrates, synthetic organic compounds, or inorganic compounds. Examples of elements which are included in a formulation are lipids capable of forming liposomes, cationic lipids, hydrophilic polymers, polycations (e.g. protamine, polybrine, spermidine, polylysine), peptide or synthetic ligand recognizing receptors on the surface of the target cells, peptide or synthetic ligand capable of inducing endosomal-lysis, peptide or synthetic ligand capable of targeting materials to the nucleus, gels, slow release matrices, salts, carbohydrates, nutrients, or soluble or insoluble particles as well as analogues or derivatives of such elements. This includes formulation elements enhancing the delivery, uptake, stability, and/or expression of genetic material into cells. This list is included for illustration only and is not intended to be limiting in any way.

The term "organism" as used herein refers to common usage by one of ordinary skill in the art. The organism can include; micro-organisms, such as yeast or bacteria, plants, birds, reptiles, fish or mammals. The organism can be a companion animal or a domestic animal. Preferably the organism is a mammal and is therefore any warm blooded organism. More preferably the mammal is a human.

The term "companion animal" as used herein refers to those animals traditionally treated as "pets" such as for example, dogs, cats, horses, birds, reptiles, mice, rabbits, hamsters, and the like.

The term "domestic animal" as used herein refers to those animals traditionally considered domesticated, where animals such as those considered "companion animals" are included along with animals such as, pigs, chickens, ducks, cows, goats, lambs, and the like.

In another embodiment the method results in an immune response, preferably a humoral immune response targeted for the protein product encoded by the nucleic acid molecule, such as an antibody response. In other situations the immune response preferably is a cytotoxic T-lymphocyte response.

The term "immune response" as used herein refers to the mammalian natural defense mechanism which can occur when foreign material is internalized. The immune response can be a global immune response involving the immune system components in their entirety. Preferably the immune response results from the protein product encoded by the formulated nucleic acid molecule. The immune response can be, but is not limited to; antibody production, T-cell proliferation/differentiation, activation of cytotoxic T-lymphocytes, and/or activation of natural killer cells. Preferably the immune response is a humoral immune response. However, as noted above, in other situations the immune response, preferably, is a cytotoxic T-lymphocyte response.

The term "humoral immune response" refers to the production of antibodies in response to internalized foreign material. Preferably the foreign material is the protein product encoded by a formulated nucleic acid molecule.

In a preferred embodiment the method results in enhanced transfection of cells. The enhanced transfection can be measured by transfection reporter methods commonly known in the art such as, for example, assays for CAT gene product activity, or LacZ gene product activity, and the like.

The term "effective amount" as used herein refers to sufficient vector administered to humans, animals or into tissue culture to produce the adequate levels of protein or RNA. One skilled in the art recognizes that the adequate level of protein or RNA will depend on the use of the particular vector. These levels will be different depending on the type of administration and treatment or vaccination.

The methods for treating diseases as disclosed herein includes treatment with biological products (specifically proteins as defined above) in which the disease being treated requires the protein to circulate through the body from the general circulation. For example, disorders which might be treated by the present invention include osteoporosis by expression of GHRH or its binding proteins. The selection of the appropriate protein to treat various diseases will be apparent to one skilled in the art.

In treating disease, the present invention provides a means for achieving: (1) sufficiently high levels of a particular protein to obtain a therapeutic effect; (2) controlled expression of product at levels which are sufficient for therapeutic effect and lower than the toxic levels; (3) controlled expression in certain tissues in order to obtain reproducible pharmacokinetics and levels of gene expression; and (4) delivery using clinically and pharmaceutically acceptable means of administration and formulation rather than transplantation of genetically engineered and selected cells.

In a ninth aspect, the invention features a homogenous mixture that is a plurality of any of the above-specified complexes where each complex has particles of substantially uniform size. In a preferred embodiment each of the complexes will have particles which are approximately spherical and which have a diameter of preferably 500 nm or less, more preferably 200 nm or less, -most preferably 100 nm or less.

In another aspect the invention features a kit. The kit includes a formulated nuclic acid complex of the invention, preferably in a container and/or with instructions explaining how to deliver the formulated nucleic acid molecules.

Thus, the "container" can include instructions furnished to allow one of ordinary skill in the art to use the formulated nucleic acid molecules. The instructions will furnish steps to use the formulated nucleic acid molecules. Additionally, the instructions may include methods for testing the formulated nucleic acid molecules that entail establishing if the formulated nucleic acid molecules are damaged. The kit may also include notification of an FDA approved use and instructions.

In another aspect, the invention features a method for making a kit. Preferably the method involves the step of combining a container with a nucleic acid formulated with a formulating agent and/or instructions.

In another aspect the invention features cells transfected or transformed with the formulated nucleic acid complex of the invention and methods of making and using the same.

The term "transfection" as used herein refers to the process of introducing DNA (e.g., formulated DNA expression vector) into a cell, thereby, allowing cellular transformation. Following entry into the cell, the transfected DNA may: (1) recombine with that of the host; (2) replicate independently as a plasmid or temperate phage; or (3) be maintained as an episome without replication prior to elimination.

As used herein, "transformation" relates to transient or permanent changes in the characteristics (expressed phenotype) of a cell induced by the uptake of a vector by that cell. Genetic material is introduced into a cell in a form where it expresses a specific gene product or alters the expression or effect of endogenous gene products.

Transformation of the cell may be associated with production of a variety of gene products including protein and RNA. These products may function as intracellular or extracellular structural elements, ligands, hormones, neurotransmitters, growth regulating factors, enzymes, chemotaxins, serum proteins, receptors, carriers for small molecular weight compounds, drugs, immunomodulators, oncogenes, cytokines, tumor suppressors, toxins, tumor antigens, antigens, antisense inhibitors, triple strand forming inhibitors, ribozymes, or as a ligand recognizing specific structural determinants on cellular structures for the purpose of modifying their activity. This list is only an example and is not meant to be limiting.

The summary of the invention described above is non-limiting and other features and advantages of the invention will be apparent from the following detailed description of the preferred embodiments, as well as from the claims.

Figure 1:
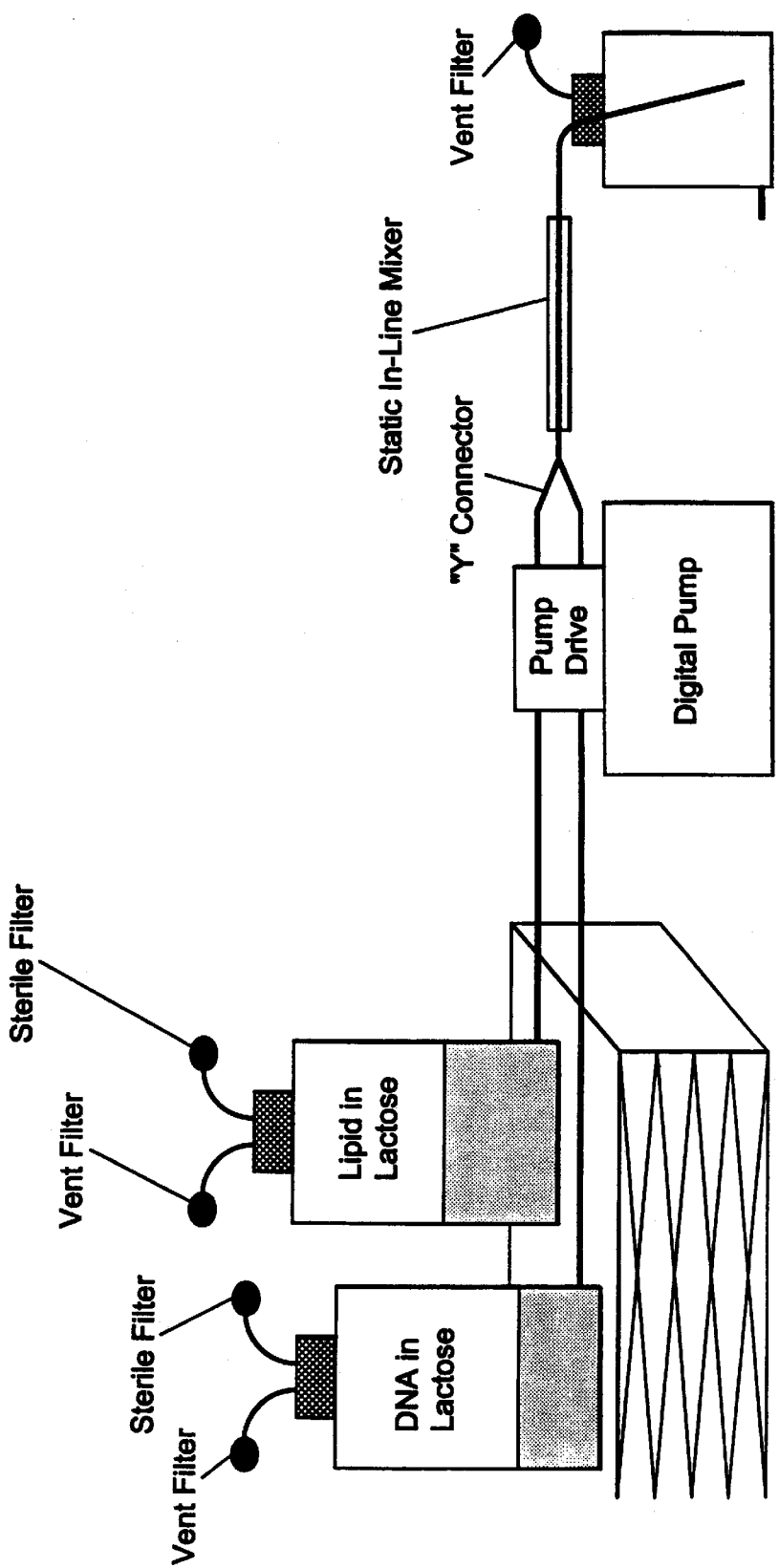
FIG. 1 is an illustration of the preferred set-up for the in-line mixing apparatus in the present invention. The two liquids are fed in to the inlets and are driven by a pump to the "Y-connector". Once the two liquids have been brought into contact they are run through a static mixer to produce a homogenous complex with particles of approximately uniform size.
Figure 2:
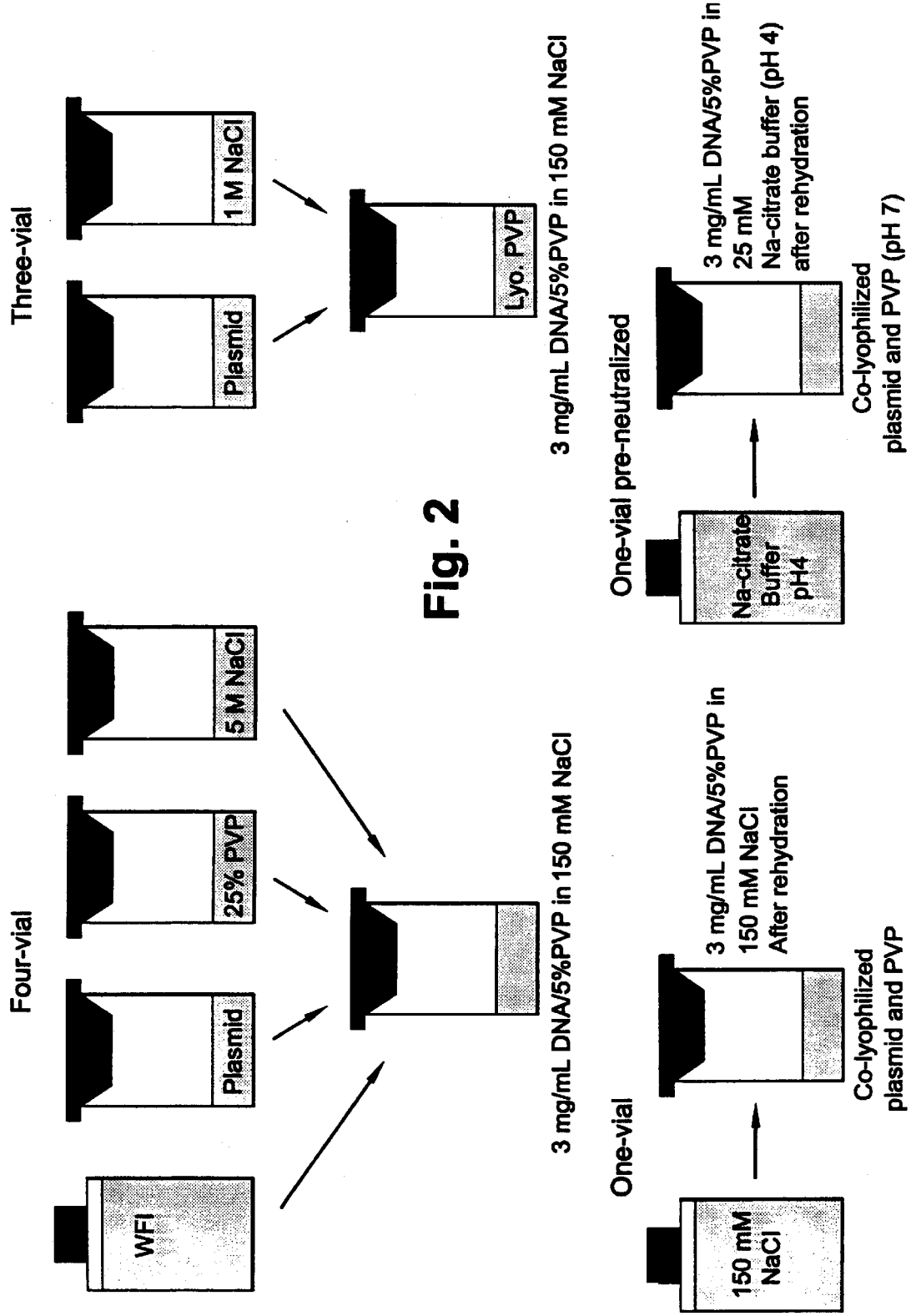
FIG. 2 is a diagram comparing the different types of multiple vial reactions to create a plasmid-containing dosage from a plasmid/PINC complex, as set forth in the Examples. In a four-vial complex, a dosage may be made by combining the four elements of WFI, plasmid, 25% PVP and NaCl just prior to administration. In a three-vial complex, the elements of plasmid and NaCl are combined with lyophilized PVP, just prior to administration. In a one-vial complex, NaCl is added to a co-lyophilized plasmid/PVP complex, to re-hydrate it prior to administration. In the one-vial pre-neutralized complex, Na-citrate buffer at a pH of 4 is added to re-hydrate a co-lyophilized plasmid/PVP complex, which has a pH of 7, just prior to administration.

The drawings are not necessarily to scale. Certain features of the invention may be exaggerated in scale or shown in schematic form in the interest of clarity and conciseness.

DETAILED DESCRIPTION OF THE PREFERRED EMBODIMENTS

The present invention, as noted above, relates generally to the incorporation of plasmid into a conventional dosage form, and more particularly to the production of a single-vial, homogenized, plasmid/polymer complex with desirable physical characteristics. Methods of making, storing and using such a complex are also provided and described in detail below. Such products and methods will provide more convenient and cost-effective complexes, which will be protected against chemical degradation and/or physical aggregation of its components and will provide for relative ease of administration. Thus, the present invention provides a more efficient complex for plasmid delivery and a method of incorporation of that plasmid into a conventional dosage form.

I. Preparation of the Formulations.
A. In-line Mixing.

The mixing method preferably is performed generally as set forth herein. Mixing of complexes, such as a DNA/lipid formulation, may be done by many ways. It is traditionally or conventionally done by simply mixing the two together. This is effective to mix the two, but the resulting complex has particles of varying size. Thus, mixing of complexes using in-line mixing will result in a more homogenous mixture, with particles of more uniform size.

There are many types of in-line mixers, most of which are generally characterized by the fact that the two liquids being mixed are in contact with one another for a short period of time. When liquids are mixed in-line, the addition of liquid can take place by many different methods. In a jet mixer, one of the liquids is pumped into a flowing stream of the other liquid and both liquids are pumped. In injectors, the flow of one liquid is induced by the flow of another, with only the majority liquid being pumped at a relatively high velocity. Another type of in-line mixing pumps both liquids through constrictions in a pipe and the pressure drop is partly utilized to create the dispersion. The constrictions can be orifices or nozzles, either singly or in a series. The use of valves can make an orifice mixer adjustable. Generally in in-line mixing the liquids are pumped. Most extensive is the use of the centrifugal pump, in which the liquids are fed into the suction side of the pump. *Perry's Chemical Engineers' Handbook*, §21, p. 57–59 ($6^{th}$ Ed. 1984).

The in-line mixer in the present invention may include an apparatus with two inlets in a Y-shape coming together to mix the two liquids. The liquids are added to the inlets and when the two liquids meet, they are shortly thereafter mixed, preferably by a static mixing. Static mixing is used because it is controllable, scalable, and reproducible. The conventional batch-fed method of mixing does not result in a continuous or scalable result.

B. Nucleic Acid Formulations.

Formulations of nucleic acid molecules can be prepared as disclosed herein and generally, a weight to weight ratio of between (1:30) and (1:1), preferably between 1:20 and 1:7, more preferably about 1:17 or about 1:10 of the plasmid and the formulating agent is used. Delivery and expression of nucleic acids in many formulations, such as in saline, is limited due to degradation of the nucleic acids by cellular components of organisms, such as for instance nucleases. Thus, protection of the nucleic acids when delivered in vivo can greatly enhance the resulting expression, and thereby enhance a desired pharmacological or therapeutic effect. It was found that certain types of compounds that interact with a nucleic acid (e.g., DNA) in solution but do not condense the nucleic acid provide in vivo protection to the nucleic acid, and correspondingly enhance the expression of an encoded gene product. Some of these compounds have been discussed in Smith et al., U.S. Pat. No. 08/484,777, filed Jun. 7, 1995, entitled "Nucleic Acid Transporters for Delivery of Nucleic Acids into a Cell" Smith et al., International Patent Application No. PCT/US96/05679 filed April 23, 1996, entitled "Nucleic Acid Transporters for Delivery of Nucleic Acids into a Cell" and Wadwah et al., U.S. Patent Application Serial No. 60/045,295, filed May 2, 1997, entitled "Transporters for Specific Delivery of Macromolecules to Cells" all of which are incorporated herein by reference in their entirety including any drawings.

The use of delivery systems designed to interact with plasmids and protect plasmids from rapid extracellular nuclease degradation are described in, Mumper, R. J., et al., 1996, *Pharm. Res.* 13:701–709. A characteristic of the PINC systems is that they are non-condensing systems that allow the plasmid to maintain flexibility and diffuse freely throughout the muscle while being protected from nuclease degradation. While the PINC systems are primarily discussed below, it will be understood that cationic lipid based systems and systems utilizing both PINCs and cationic lipids are also within the scope of the present invention.

A common structural component of the PINC systems is that they are amphiphilic molecules, having both a hydrophilic and a hydrophobic portion. The hydrophilic portion of the PINC is meant to interact with plasmids by hydrogen bonding (via hydrogen bond acceptor or donor groups), Van der Waals interactions, and/or by ionic interactions. For example, PVP and N-methyl-2-pyrrolidone (NM2P) are hydrogen bond acceptors while PVA and Propylene Glycol (PG) are hydrogen bond donors.

All four molecules have been reported to form complexes with various (poly)anionic molecules [Buhler V., BASF Aktiengescellschaft Feinchemie, Ludwigshafen, pp 39–42; Galaev Y, et al., *J. Chrom. A.* 684:45–54 (1994); Tarantino R, et al. *J. Pharm. Sci.* 83:1213–1216 (1994); Zia, H., et al., *Pharm. Res.* 8:502–504 (1991);]. The hydrophobic portion of the PINC systems is designed to result in a coating on the plasmid rendering its surface more hydrophobic. Kabanov et al. have described previously the use of cationic polyvinyl derivatives for plasmid condensation designed to increase plasmid hydrophobicity, protect plasmid from nuclease degradation, and increase its affinity for biological membranes [Kabanov, A. V., and Kabanov, V. A., 1995, *Bioconj. Chem.* 6:7–20; Kabanov, A. V., et al., 1991, *Biopolymers* 31:1437–1443; Yaroslavov, A. A., et al., 1996, *FEBS Letters* 384:177–180].

1. Summary of Interactions Between a PINC Polymer (PVP) and Plasmid

While expression systems such as those described above provide the potential for expression when delivered to an appropriate location, it is beneficial to provide the expression system construct(s) in a delivery system which can assist both the delivery and the cellular uptake of the construct. Thus, this invention also provides particular formulations that include one or more expression system constructs (e.g., DNA plasmids as described above), and a protective, interactive non-condensing compound.

An additional significant factor relating to the plasmid construct is the percentage of plasmids that are in a supercoiled (SC) form rather than the open circular (OC) form.

Molecular modeling has demonstrated that an exemplary PINC polymer, PVP, forms hydrogen bonds with the base pairs of a plasmid within its major groove and results in a hydrophobic surface on the plasmid due to the vinyl backbone of PVP. These interactions are supported by the modulation of plasmid zeta potential by PVP as well as by the inhibition of ethidium bromide intercalation into complexed plasmid. Apparent binding between PVP and plasmid has been correlated to pH and salt concentration and have demonstrated the effect of these parameters on β-gal expression after intramuscular injection of plasmid/PVP complexes [Mumper, R. J., et al., 1997. Submitted to *Gene Therapy*]. A summary of the physico-chemical properties of plasmid/PVP complexes is listed in Table I below.

TABLE 1

Summary of the Physico-Chemical Properties of Plasmid/PVP Complexes

| Method | Result |
| --- | --- |
| Molecular modeling plasmid surface observed | Hydrogen bonding and hydrophobic |
| Fourier-transformed Infra-red | Hydrogen bonding demonstrated |
| DNase I challenge | Decreased rate of plasmid degradation in the presence of PVP |
| Microtitration Calorimetry | Positive heats of reaction indicative of an endothermic process |
| Potentiometric titration | One unit pH drop when plasmid and PVP are complexed |
| Dynamic Dialysis | Rate of diffusion of PVP reduced in the presence of plasmid |
| Zeta potential modulation | Surface charge of plasmid decreased by PVP |
| Ethidium bromide Intercalation by plasmid/PVP complexation | Ethidium bromide intercalation reduced |
| Osmotic pressure | Hyper-osmotic formulation (i.e., 340 mOsm/kg $H_2O$) |
| Luminescence Spectroscopy | Plasmid/PVP binding decreased in salt and/or at pH 7 |

2. Histology of Expression in Muscle

Immunohistochemistry for β-gal using a slide scanning technology has revealed the uniform distribution of β-gal expression sites across the whole cross-sections of rat tibialis muscles very localized areas were stained positive for β-gal when CMV-β-gal plasmid was formulated in saline. β-gal positive cells were observed exclusively around the needle tract when plasmid was injected in saline. This is in agreement with previously published results [Wolff, J. A., et al., 1990, *Science* 247:1465–68; Davis, H. L., et al., 1993, *Hum. Gene Ther.* 4:151–9; Davis, H. L., et al., 1993, *Hum. Gene Ther.* 4:733–40].

In comparison, immunoreactivity for β-gal was observed in a wide area of muscle tissue after intramuscular injection of CMV-β-gal plasmid/PVP complex (1:17 w/w) in 150 mM NaCl. It appeared that the majority of positive muscle fibers were located at the edge of muscle bundles. Thus, staining for β-gal in rat muscle demonstrated that, using a plasmid/PVP complex, the number of muscle fibers stained positive for β-gal was approximately 8-fold greater than found using a saline formulation. Positively stained muscle fibers were also observed over a much larger area in the muscle tissue using the plasmid/PVP complex providing evidence that the injected plasmid was widely dispersed after intramuscular injection.

One conclusion is that the enhanced plasmid distribution and expression in rat skeletal muscle was a result of both protection from extracellular nuclease degradation due to complexation and hyper-osmotic effects of the plasmid/PVP complex. However, Dowty and Wolff et al. have demonstrated that osmolarity, up to twice physiologic osmolarity, did not significantly affect gene expression in muscle [Dowty, M. E., and Wolff, J. A. In: J. A. Wolff (Ed.), 1994, *Gene Therapeutics: Methods and Applications of Direct Gene Transfer*. Birkhauser, Boston, pp. 82–98]. This suggests that the enhanced expression of plasmid due to PVP complexation is most likely due to nuclease protection and less to osmotic effects. Further, the surface modification of plasmids by PVP (e.g., increased hydrophobicity and decreased negative surface charge) may also facilitate the uptake of plasmids by muscle cells.

3. Structure-activity Relationship of PINC Polymers

A linear relationship between the structure of a series of co-polymers of vinyl pyrrolidone and vinyl acetate and the levels of gene expression in rat muscle has been found. Also, the substitution of some vinyl pyrrolidone monomers with vinyl acetate monomers in PVP results in a co-polymer with reduced ability to form hydrogen bonds with plasmids. The reduced interaction subsequently led to decreased levels of gene expression in rat muscle after intramuscular injection. The expression of β-gal decreased linearly (R=0.97) as the extent of vinyl pyrrolidone monomer (VPM) content in the co-polymers decreased.

These data demonstrate that pH and viscosity are not the most important parameters effecting delivery of plasmid to muscle cells since these values were equivalent for all complexes. These data suggest that enhanced binding of the PINC polymers to plasmid results in increased protection and bioavailability of plasmid in muscle.

4. Additional PINC Systems

The structure-activity relationship described above can be used to design novel co-polymers that will also have enhanced interaction with plasmids. It is expected that there is "an interactive window of opportunity" whereby enhanced binding affinity of the PINC systems will result in a further enhancement of gene expression after their intramuscular injection due to more extensive protection of plasmids from nuclease degradation. It is expected that there will be an optimal interaction beyond which either condensation of plasmids will occur or "triplex" type formation, either of which can result in decreased bioavailability in muscle and consequently reduced gene expression.

As indicated above, the PINC compounds are generally amphiphilic compounds having both a hydrophobic portion and a hydrophilic portion. In many cases the hydrophilic portion is provided by a polar group. It is recognized in the art that such polar groups can be provided by groups such as, but not limited to, pyrrolidone, alcohol, acetate, amine or heterocyclic groups such as those shown on pp. 2-73 and 2-74 of CRC Handbook of Chemistry and Physics (72nd Edition), David R. Lide, editor, including pyrroles, pyrazoles, imidazoles, triazoles, dithiols, oxazoles, (iso)thiazoles, oxadiazoles, oxatriazoles, diaoxazoles, oxathioles, pyrones, dioxins, pyridines, pyridazines, pyrimidines, pyrazines, piperazines, (iso)oxazines, indoles, indazoles, carpazoles, and purines and derivatives of these groups, hereby incorporated by reference.

Compounds also contain hydrophobic groups which, in the case of a polymer, are typically contained in the backbone of the molecule, but which may also be part of a non-polymeric molecule. Examples of such hydrophobic backbone groups include, but are not limited to, vinyls, ethyls, acrylates, acrylamides, esters, celluloses, amides, hydrides, ethers, carbonates, phosphazenes, sulfones, propylenes, and derivatives of these groups. The polarity characteristics of various groups are quite well known to those skilled in the art as illustrated, for example, by discussions of polarity in any introductory organic chemistry textbook.

The ability of such molecules to interact with nucleic acids is also understood by those skilled in the art, and can be predicted by the use of computer programs which model such intermolecular interactions. Alternatively or in addition to such modeling, effective compounds can readily be identified using one or more of such tests as 1) determination of inhibition of the rate of nuclease digestion, 2) alteration of the zeta potential of the DNA, which indicates coating of DNA, 3) or inhibition of the ability of intercalating agents, such as ethidium bromide to intercalate with DNA.

5. Targeting Ligands

In addition to the nucleic acid/PINC complexes described above for delivery and expression of nucleic acid sequences, in particular embodiments it is also useful to provide a targeting ligand in order to. preferentially obtain expression in particular tissues, cells, or cellular regions or compartments.

Such a targeted PINC complex includes a PINC system (monomeric or polymeric PINC compound) complexed to plasmid (or other nucleic acid molecule). The PINC system is covalently or non-covalently attached to (bound to) a targeting ligand (TL) which binds to receptors having an affinity for the ligand. Such receptors may be on the surface or within compartments of a cell. Such targeting provides enhanced uptake or intracellular trafficking of the nucleic acid.

The targeting ligand may include, but is not limited to, galactosyl residues, fucosal residues, mannosyl residues, carnitine derivatives, monoclonal antibodies, polyclonal antibodies, peptide ligands, and DNA-binding proteins. Examples of cells which may usefully be targeted include, but are not limited to, antigen-presenting cells, hepatocytes, myocytes, epithelial cells, endothelial cells, and cancer cells.

Formation of such a targeted complex is illustrated by the following example of covalently attached targeting ligand (TL) to PINC system:

Formation of such a targeted complex is also illustrated by the following example of non-covalently attached targeting ligand (TL) to PINC system

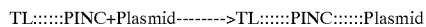

or alternatively,

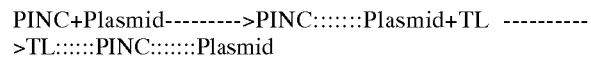

In these examples :::::::::: is non-covalent interaction such as ionic, hydrogen-bonding, Van der Waals interaction, hydrophobic interaction, or combinations of such interactions.

A targeting method for cytotoxic agents is described in Subramanian et al., International Application No. PCT/US96/08852, International Publication No. WO 96/39124, hereby incorporated by reference. This application describes the use of polymer affinity systems for targeting cytotoxic materials using a two-step targeting method involving zip polymers, i.e., pairs of interacting polymers. An antibody attached to one of the interacting polymers binds to a cellular target. That polymer then acts as a target for a second polymer attached to a cytotoxic agent. As referenced in Subramanian et al., other two-step (or multi-step) systems for delivery of toxic agents are also described.

In another aspect, nucleic acid coding sequences can be delivered and expressed using a two-step targeting approach involving a non-natural target for a PINC system or PINC-targeting ligand complex. Thus, for example, a PINC-plasmid complex can target a binding pair member which is itself attached to a ligand which binds to a cellular target (e.g., a MAB). Binding pairs for certain of the compounds identified herein as PINC compounds as identified in Subramanian et al. Alternatively, the PINC can be complexed to a tareting ligand, such as an antibody. That antibody can be targeted to a non-natural target which binds to, for example, a second antibody.

C. Storage of the Resulting plasmid/PINC Complex

Often there is a need to make the plasmid/PINC complex well before administration. Lyophilzation may be used to store the complex in a form that minimizes the reduction of the biological activity of the plasmid.

In the process of lyophilization, essentially freeze-drying, the complex is subjected to lower pressures at which the vaporization points of the solvents are also reduced and the liquid is removed at that lower temperature. Additional detail regarding the lyophilization process can be found in the references incorporated by reference in the summary of the invention section above.

D. Nature of Nucleic Acid

The nucleic acid molecules, in some aspects and embodiments, have been isolated, purified or enriched.

By "isolated" in reference to nucleic acid is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90-95% pure at least) of non-nucleotide material naturally associated with it and thus is meant to be distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19.

This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does to require absolute purity such as a homogeneous preparation); instead, it represents an indication that the sequence is relatively purer than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus purification of at least one order of magnitude, preferably two or three orders, and more preferably four or five orders of magnitude is expressly contemplated. The term is also chosen to distinguish clones already in existence but which have not been isolated from other clones in a library of clones.

IV. Features of Preferred Plasmids and Vectors of the Invention.

The present invention relates to a recombinant DNA molecules comprising a vector and a nucleic acid molecule described herein. The above-described molecules may be isolated and/or purified DNA molecules.

The present invention also relates to a promoter linked to a coding sequence as described herein and thereby is capable of expressing a peptide. The. polypeptide may be purified from cells which have been altered to express the polypeptide. A cell is said to be "altered to express a desired polypeptide" when the cell, through genetic manipulation, is made to produce a protein which it normally does not produce or which the cell normally provides at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a desired gene may be obtained by the above-described cloning methods. This region may be retained for its transcriptional termination regulatory sequences, such as termination and polyadenylation. Thus, by retaining the 3'-region naturally contiguous to the DNA sequence encoding a desired gene, the transcriptional termination signal may be provided. Where the transcriptional termination signals are not satisfactorily functional in the expression host cell, then a 3' region functional in the host cell may be substituted.

Two DNA sequences (such as a promoter region sequence and a desired sequence) are said to be operably linked in the nature of the linkage between the two DNA sequences does no (1) result in the introduction of a frame-shift mutation, (2) interfere with the ability of the promoter region sequence to direct the transcription of a desired gene sequence, or (3) interfere with the ability of the a desired gene sequence to be transcribed by the promoter region sequence. Thus, a promoter region would be operably linked to a DNA sequence if the promoter were capable of effecting transcription of that DNA sequence. Thus, to express a desired gene, transcriptional and translational signals recognized by an appropriate host are necessary.

The present invention encompasses the expression of a desired gene (or a functional derivative thereof) in either prokaryotic or eukaryotic cells. Prokaryotic hosts are, generally, very efficient and convenient for the production of recombinant proteins and are, therefore, one type of preferred expression system for a desired gene. Prokaryotes most frequently are represented by various trans of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, kgt11 and the like; and suitable virus vectors may include pMAM-neo, pKRC and the like. Preferably, the selected vector of the present invention has the capacity to replicate in the selected host cell.

Recognized prokaryotic hosts include bacteria such a *E. coli* and those from general such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express a desired gene (or a functional derivative thereof) in a prokaryotic cell, it is necessary to operably link a desired sequence to a functional prokaryotic promoter, such as the modified CMV promoter of the invention.

Proper expression in a prokaryotic cell also requires the presence of a ribosome binding site upstream of the gene sequence-encoding sequence. Such ribosome binding sites are disclosed, for example, by Gold et al. (Ann. Rev. Microbiol. 35:365–404, 1981). The selection of control sequences, expression vectors, transformation methods, and the like, are dependent on the type of host cell used to express the gene.

As used herein, "cell," "cell line," and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of a peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and opaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459, 1988). Alternatively baculovirus vectors can be engineered to express large amounts of a desired peptide or protein in insects cells (Jasny, *Science* 238:1653, 1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when years are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of desired genes.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Translation of eukaryotic mRNA is initiated at the codon which encodes the first methionine. For this reason, it is preferable to ensure that the linkage between a promoter and a DNA sequence which encodes a desired peptide or protein does not contain any intervening codons which are capable of encoding a methionine (i.e., AUG). The presence of such codons results either in a formation of a fusion protein (if the AUG codon is in the same reading frame as a desired coding sequence) or a frame-shift mutation (if the AUG codon is not in the same reading frame as a desired coding sequence).

A desired nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Bio.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColEl, pSC101, pACYC 184, pVX. Such plasmids are, for example, disclosed by Sambrook (cf. "Molecular Cloning: A Laboratory Manual," second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include plJ101 (Kendall et al., *J. Bacteriol.* 169:4177–4183, 1987), and streptomyces bacteriophages such as fC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704, 1986), and Izaki (*Jpn. J. Bacteriol.* 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982); Broach, In: "The Molecular Biology of the Yeast Saccharomyces: Life Cycle and Inheritance," Cold Spring Harbor Laboratory, Cold Spring Harbor, N.Y., p. 445–470 (1981); Broach, *Cell* 28:203–204, 1982); Bollon et al., *J. Clin. Hematol. Oncol.* 10:39–48, 1980); Maniatis, In : Cell Biology: A Comprehensive Treatise, Vol. 3, Gene Sequence Expression, Academic Press, NY, pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of the desired peptide or protein. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

The methods of formulating described herein would be appropriate for use with a wide variety of genes and plasmids, including IL-2, IL-12, interferon-alpha, and IGF-1 as respectively described in Ralston et al., U.S. patent application Ser. No. 09/012,366, entitled "IL-2 Gene Expression and Delivery Systems and Uses", filed Jan. 23, 1998 Nordstrom et al, U.S. patent application Ser. No. 08/949,160, entitled "IL-12 Gene Expression and Delivery Systems and Uses", filed Oct. 10, 1997 Nordstrom et al., U.S. Patent Application Serial No. 60/078,654, entitled "Interferon Alpha and Delivery Systems, and Methods of Making and Using the Same", filed Mar. 19, 1998 and Coleman et al. U.S. patent application Ser. No. 08/974,572, entitled "IGF-I Expression System and Methods of Use", filed Nov, 19, 1997, all of which are hereby incorporated herein by reference in their entirety, including drawings VI. Administration.

Administration as used herein refers to the route of introduction of a vector or carrier of DNA into the body. Administration can be directly to a target tissue or by targeted delivery to the target tissue after systemic administration. In particular, the present invention can be used for treating disease by administration of the vector to the body in order to establishing controlled expression of any specific nucleic acid sequence within tissues at certain levels that are useful for gene therapy.

The preferred means for administration of vector and use of formulations for delivery are described above. The preferred embodiment is by direct injection using needle injection or hypospray.

The route of administration of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

Muscle cells have the unique ability to take up DNA from the extracellular space after simple injection of DNA particles as a solution, suspension, or colloid into the muscle. Expression of DNA by this method can be sustained for several months.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determines the bioavailability of the vector within the body. Other elements of the formulation function as ligand which interact with specific receptors on the surface or interior of the cell. Other elements of the formulation function to enhance entry into the cell, release from the endosome, and entry into the nucleus.

Delivery can also be through use of DNA transporters. DNA transporters refers to molecules which bind to DNA vectors and are capable of being taken up by epidermal cells. DNA transporters contain a molecular complex capable of noncovalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Ser. No. 07/855,389, filed Mar. 20, 1992, entitled "A DNA Transporter System and Method of Use now abandoned; (2) Woo et al., PCT/US93/02725 filed Mar. 19, 1993, International Publ. WO93/18759, entitled "A DNA Transporter System and method of Use", (designating the U.S. and other countries) (3) a continuation-in-part application by Woo et al., U.S. Ser. No. 08/167,641, filed Dec. 14, 1993, entitled "Nucleic Acid Transporter Systems and Methods of Use" (4) Szoka et al., U.S. Ser. No. 07/913,669, filed Jul. 14, 1992, entitled "Self-Assembling Polynucleotide Delivery System"; and (5) Szoka et al., PCT/US93/03406, filed Apr. 5, 1993, International Publ. WO93/19768 entitled "Self-Assembling Polynucleotide Delivery System", (designating the U.S. and other countries).

Transfer of genes directly into muscle has been very effective. Experiments show that administration by direct injection of DNA into muscle cells results in expression of the gene in the area of injection. Injection of plasmids containing GHRH results in expression of the gene for months at relatively constant levels. The injected DNA appears to persist in an unintegrated extrachromosomal state. This means of transfer is the preferred embodiment.

Another preferred method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. One element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblasts genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs gene therapy and the genetically engineered cells can also be easily put back with out causing damage to the patient's muscle. Similarly, keratinocytes may be used to deliver genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the E1 region of the virus genome with the vector elements described in this invention including promoter, 5' UTR, 3' UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

The chosen method of delivery should result in expression of the gene product encoded within the nucleic acid cassette at levels which exert an appropriate biological effect. The rate of expression will depend upon the disease, the pharmacokinetics of the vector and gene product., and the route of administration, but should be between 1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

VII. Cell Transfection and Transformation

As used herein, "transformation" preferably is the change in a cell's phenotypic characteristics by the action of a gene expressing a gene product. The gene causing the phenotypic characteristic change has been transfected into the cell.

The term "transfection" as used herein preferably refers to a mechanism of gene transfer which involves the uptake of DNA by a cell or organism. Following entry into the cell, the transforming DNA may recombine with that of the host by physically integrating into the chromosomes of the host cell, may be maintained transiently as an episomal element without being replicated, or may replicate independently as a plasmid. Preferably the transforming DNA does not integrate.

Transfection can be performed by in vivo techniques as described below, or by ex vivo techniques in which cells are co-transfected with a vector containing a selectable marker. This selectable marker is used to select those cells which have become transformed. It is well known to those skilled in the art the type of selectable markers to be used with transfection/transformation studies. An example of such a marker is a neo gene, providing neomycin/kanamycin resistance.

Transfection/transformation can be tissue-specific, i.e., involve the use of myogenic specific vectors which cause expression of the nucleic acid cassette predominantly in the tissue of choice. In particular, tissue specificity can be directed to myogenic cells by using a promoter and/or 3' UTR and/or 3' NCR sequences specific for myogenic tissue expression.

One aspect of the present invention includes cells transfected with the vectors described above. Once the cells are transfected, the transformed cells will express the protein or RNA encoded for by the nucleic acid cassette. Examples of proteins include, but are not limited to polypeptide, glycoprotein, lipoprotein, phosphoprotein, or nucleoprotein.

The nucleic acid cassette which contains the genetic material of interest is positionally and sequentially oriented within the vectors such that the nucleic acid in the cassette can be transcribed into RNA and, when necessary, be translated into proteins or polypeptides in the transformed cells.

A variety of proteins can be expressed by the sequence in the nucleic acid cassette in the transformed cells. Those proteins which can be expressed may be located in the cytoplasm, nucleus, membranes (including the plasmalemma, nuclear membrane, endoplasmic reticulum or other internal membrane compartments), in organelles (including the mitochondria, peroxisome, lysosome, endosome or other organelles), or secreted. Those proteins may function as intracellular or extracellular structural elements, ligand, hormones, neurotransmitter, growth regulating factors, differentiation factors, gene-expression regulating factors, DNA-associated proteins, enzymes, serum proteins, receptors, carriers for small molecular weight organic or inorganic compounds, drugs, immunomodulators, oncogenes, tumor suppressor, toxins, tumor antigens, or antigens. These proteins may have a natural sequence or a mutated sequence to enhance, inhibit, regulate, or eliminate their biological activity. A specific example of a protein to be expressed is hGHRH.

In addition, the nucleic acid cassette can code for RNA. The RNA may function as a template for translation, as an antisense inhibitor of gene expression, as a triple-strand forming inhibitor of gene expression, as an enzyme (ribozyme) or as a ligand recognizing specific structural determinants on cellular structures for the purpose of modifying their activity. Specific examples include RNA molecules to inhibit the expression or function of prosta-gladin synthase, lipooxenganse, histocompatibilty antigens (class I or class II), cell adhesion molecules, nitrous oxide synthase, $\beta_2$ microglobulin, oncogenes, and growth factors.

The compounds which can be incorporated are only limited by the availability of the nucleic acid sequence for the protein or polypeptide to be incorporated. One skilled in the art will readily recognize that as more proteins and polypeptides become identified they can be integrated into the vector system of the present invention and expressed in animal or human tissue.

Transfection can be done either by in vivo or ex vivo techniques. For example, muscle cells can be propagated in culture, transfected with the transforming gene, and then transplanted into muscle tissue. Alternatively, the vectors can be administered to the cells by the methods discussed above.

A variety of proteins or their genetic sequences, both mutated and non-mutated, will also be useful in gene therapy (reviewed in Miller, Nature 357:455–460, (1992). Miller states that advances have resulted in practical approaches to human gene therapy that have demonstrated positive initial results. The basic science of gene therapy is described in Mulligan, Science 260:926–931, (1993).

In one preferred embodiment, an expression vector containing coding sequence is inserted into cells, the cells are grown in vitro and then infused in large numbers into patients. In another preferred embodiment, a DNA segment containing a promoter of choice (for example a strong promoter) is transferred into cells containing an endogenous desired gene in such a manner that the promoter segment enhances expression of the endogenous desired gene (for example, the promoter segment is transferred to the cell such that it becomes directly linked to the endogenous desired gene).

The gene therapy may involve the use of an adenovirus containing desired gene cDNA targeted to an appropriate cell type, systemic desired gene increase by implantation of engineered cells, injection with desired gene virus, or injection of naked desired gene DNA into appropriate cells or tissues, for example neurons.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant protein into the targeted cell population (e.g., tumor cells or neurons). Methods which are well known to those skilled in the art can be used to construct recombinant viral vectors containing coding sequences. See, for example, the techniques described in Maniatis et al., Molecular cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (see e.g., Felgner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. (Capecchi MR, Cell 22:479–88), 1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with CaPO$_4$ and taken into cells by pinocytosis (Chen C. and Okayama H, *Mol. Cell Biol.* 7:2745–52, 1987); electroporation, wherein cells are exposed to large voltage pulses to introduce holes into the membrane (Chu G., et al., *Nucleic Acids Res.,* 15:1311–26, 1987); lipofection/ liposome fusion, wherein DNA is packaged into lipophilic vesicles which fuse with a target cell (Felgner PL., et al., *Proc. Natl. Acad. Sci. USA.* 84:7413–7, 1987)); and particle bombardment using DNA bound to small projectiles (Yang N.S. et al., *Proc. Natl. Acad. Sci., USA* 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D. T. et al., *Am. J. Respir. Cell. Mol. Biol.,* 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding a desired protein is provided in which the nucleic acid sequence is expressed only in specific tissue. Methods of achieving tissue-specific gene expression as set forth in Schwartz, et al., International Application No. PCT/US92/09353, International Publication No. WO 93/09236, filed Nov. 3, 1992 and published May 13, 1993 entitled "Myogenic Vector Systems"

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

VIII. Treatments and Uses of the Complexes.

The present invention may be used to treat a wide variety of diseases, depending on the selected vector. Different vectors correspond to the treatment of different diseases, as listed below. The following list is not meant to limit the invention in any way.

TABLE 2

Applications for Plasmid-Based Gene Therapy by Intramuscular Injection

| | References are numbered as they are cited in U.S. application Ser. No. PCT/US96/05679, which has been incorporated by reference in its entirety. |
|---|---|
| Muscle and nerve disorders | |
| Duchenne's muscular dystrophy | Acsadi 1991 [5], Karpati 1993 [6], Miller 1995 [7] |
| Myotrophic disorders (IGF-I) | Coleman 1997 [8], Alila 1997 [9] |
| Neurotrophic disorders (IGF-I) | Alila 1997 [9], Rabinovsky 1997 [10] |
| Secretion of expressed protein into the systemic circulation | |
| Hemophilias A and B | Anwer 1996 [11], Kuwahara-Rundell 1994 [12], Miller 1994 [13] |
| Erythropoietin-responsive | Tripathy 1996 [14] |
| Pituitary dwarfism | Anwer 1996 [11], Dahler 1994 [15] |
| α1-Antitrypsin deficiency | Levy 1996 [16] |
| Autoimmune and Inflammatory diseases | Raz 1993 [17] |
| Hypercholesterolema | Fazio 1994 [18] |
| Hypotension | Ma 1995 [19] |
| Hypertension | Xiong 1995 [20] |
| Nucleic acid vaccines | |
| Herpes Simplex Virus | Manickan 1995 [21], Ghiasi 1995 [22], McClements 1996 [23], Kriesel 1996 [24] |
| Hepatitis B Virus | Davis 1993 [25], Davis 1994 [26], Davis 1996 [27] |
| Influenza Virus | Donnelly 1995 [28], Ulmer 1993 [29], Ulmer 1994 [30] |
| Tuberculosis | Lowrie 1994 [31], Tascon, 1996 [32] |
| Human Immunodeficiency Virus | Shiver 1995 [33], Coney 1994 [34], Wang 1993 [35] |
| Cancer | Raz 1993 [17], Russell 1994 [36] |
| Malaria | Hoffman 1995 [37], Sedegah 1994 [38] |
| Hepatitis C virus | Major 1995 [39], Lagging 1995 [40] |
| Flavivirus | Phillpotts 1996 [41] |
| Cytomegalovirus | Pande 1995 [42] |
| Salmonella typhi | Lopez-Macias 1995 [43] |
| Mycoplasma pulmonis | Lai 1995 [44] |
| Rabies virus | Xiang 1995 [45] |
| Other Conditions | |
| Peripheral vascular disease | (e.g., VEGF, mcP-1, cytokine gene therapy (e.g., IL-2, IL-12, Interferon-alpha, anti-angiogenisis (e.g., angiostatin, endostatin, soluble VEGF receptor) |

The condition or disease preferably is a cancer, such as epithelial glandular cancer, including adenoma and adenocarcinoma; squamous and transitional cancer, including polyp, papilloma, squamous cell and transitional cell carcinoma; connective tissue cancer, including tissue type positive, sarcoma and other (oma's); hematopoietic and lymphoreticular cancer, including lymphoma, leukemia and Hodgkin's disease; neural tissue cancer, including neuroma, sarcoma, neurofibroma and blastoma; mixed tissues of origin cancer, including teratoma and teratocarcinoma. Other cancerous conditions that are applicable to treatment include cancer of any of the following: adrenal gland, anus, bile duct, bladder, brain tumors: adult, breast, cancer of an unknown primary site, carcinoids of the gastrointestinal tract, cervix, childhood cancers, colon and rectum, esophagus, gall bladder, head and neck, islet cell and other pancreatic carcinomas, Kaposi's sarcoma, kidney, leukemia, liver, lung: non-small cell, lung: small cell, lymphoma: AIDS-associated, lymphoma: Hodgkin's disease, Lymphomas: non-Hodgkin's disease, melanoma, mesothelioma, metastatic cancer, multiple myeloma, ovary, ovarian germ cell tumors, pancreas, parathyroid, penis, pituitary, prostate, sarcomas of bone and soft tissue, skin, small intestine, stomach, testis, thymus, thyroid, trophoblastic disease, uterus: endometrial carcinoma, uterus: uterine sarcomas, vagina, or vulva.

EXAMPLES

The present invention will be more fully described in conjunction with the following specific examples, which are not to be construed in any way as limiting the scope of the invention.

Variables affecting the long-term storage stability of plasmid/polyvinyl pyrrolidone (PVP) complexes and plasmid/polyvinyl alcohol (PVA) complexes were investigated as part of an ongoing project to develop a formulation for clinical use.

A one-vial plasmid/PVP complex (1:17 w/w) or a one-vial plasmid/PVA (1:10 w/w) is provided herein and is desirable due to (1) reduced cost of manufacturing (2) ease of manufacturing and quality control testing (3) product stability and (4) increased doctor/patient compliance and relative ease of administration. A formulation that is a one-vial, lyophilized product, which retains the same physical characteristics and potency as that of the freshly prepared four-vial complex is featured herein. While the stability and potency of the product were paramount, characteristics such as ease of preparation and re-hydration ability were also considered. Candidate complexes were analyzed for composition, plasmid topology, osmolality, pH, in vitro potency, and in vivo potency. Plasmid lyophilized in the absence of cryoprotectant results in loss of percent supercoiled fraction and increased abasic damage with concomitant loss in activity.

The addition of sugar (10% lactose) to our complexes stabilizes the complex in terms of physical form, but decreases the in vivo activity by 6-fold compared to a formulation made isotonic with 150 mM NaCl and having the same pH. Without wishing to be bound to any particular theory regarding the operation of the invention, this decrease in in vivo activity may be due to the competition between the sugar and plasmid to form hydrogen bonds with the PVP.

One of the difficulties in using PVP in a plasmid complex is that the pH of the optimal formulation is approximately 4.0 and it is well known that plasmid will degrade at this pH. Another problem associated with maintaining the plasmid at a low pH is the propensity to form abasic sites. This so-called "nicking" of the plasmid could inhibit effective transcription of the plasmid if nicks occur in the coding region. The focus of the experiments presented here is the one-vial PVP (PN) complex, however a one-vial liquid and a one-vial liquid and then frozen complex would also be feasible. The plasmid/PVA complexes have the same requirements as the plasmid/PVP complexes except that the pH of the PVA is inherently higher, ~5.75–6.0, so the plasmid degradation is not as great an issue as with PVP. An eight week one-vial plasmid/PVA stability study was completed to determine the most suitable supplier of PVA and the optimal storage conditions for the complexes (i.e. liquid, frozen, or lyophilized).

The four-vial plasmid/PVP (1:17 w/w) complex [3 mg/mL plasmid] in 150 mM NaCl was used for most of the pre-clinical experiments because it can be easily formulated in a relatively short period of time. This formulation has proven to be superior in vivo over "naked" plasmid, however, it is not stable over time at 4° C. The instability of this formulation is due to the inherent low pH of the formulation, which causes depurination of the plasmid. Depurination of the plasmid may cause a loss of biological activity of transforming plasmid. T. Lindahl and B. Nyberg, "Rate of depurination of native deoxyribonucleic acid." *Biochemistry*, Vol. 11, No. 19, 1972. Another problem with the stability of the four-vial formulation relates to the fact that, for sterilization, the 25% PVP stock solution must be autoclaved. This method can damage the PVP through an oxidative process and also lead to the formation of peroxides when can eventually damage the plasmid. For example, the $UV_{320}$ measurement for freshly made 5% PVP is approximately $\leq 0.1500$ compared to $>0.4000$ for autoclaved 25% PVP.

To develop a one-vial plasmid/PVP (1:17 w/w) formulation, the most important factors leading to plasmid degradation and to the loss of in vivo potency were determined. It was found that the pH of the formulation was an important factor in the expression levels of the animal. The formulation expressed highest when at its inherent pH of 3–4, and although the plasmid is more stable at a higher pH, the in vivo expression levels decrease significantly when the pH is raised even to 5.5.

Since it was necessary for the formulation to be at low pH (i.e., pH 3.0–4.0), the next question was how to maintain the stability of the formulations physical characteristics over time. To answer this question, a stability study was performed with several formulation candidates. The three-vial formulation was selected because the plasmid and the PVP would be in separate containers and therefore the plasmid would not be effected by the low pH of the PVP. The one-vial was selected because the lyophilization process might slow the progression of degradation and the PVP could act as a sufficient cryoprotectant. The one-vial (PN) was selected for essentially the same reasons as the one-vial, but it had an extra benefit of being stored at pH 7. The pre-neutralized PVP would prevent the plasmid from being degraded while being stored, and upon re-hydration with Na-citrate buffer (pH 4) the formulation would be active in vivo. The four-vial formulation was placed on stability as a control since most of the pre-clinical experiments were completed with this formulation, and it could serve as a baseline for the other formulations.

One of the requirements for preparing the four-vial and the three-vial formulations is that the plasmid concentration must be $\geq 4$ mg/mL so that the final plasmid concentration can be 3 mg/mL (see FIG. 1). Plasmid received at a concentration <4 mg/mL must be lyophilized and re-hydrated to the desired concentration. This process is very damaging to the plasmid and also leads to a loss of in vivo expression. The one-vial complexes have the added advantage of being able to use any starting plasmid concentration with the final product still being 3 mg/mL.

Plasmid form, or more specifically the percent of supercoiled plasmid, was an excellent indicator of stability and correlated very well with the in vivo data. The one-vial (PN) and the three-vial formulation were the only formulation to express in vivo at the six-month time point. At this six-month time point, it is clear that the two best formulations in terms of supercoiled DNA stability are the one-vial (PN) and the three-vial formulations. The data clearly shows that PVP is a sufficient cryoprotectant for plasmids in that it protects against the loss of supercoiled plasmid and abasic damage while retaining its in vivo potency.

The stability results for the one-vial plasmid/PVA complexes were quite different than the plasmid/PVP results. Lyophilized plasmid/PVA complexes were found to be difficult to re-hydrate which led to variability in viscosities from vial to vial. The pH of the complex was high enough that the plasmid was not degraded and the complexes were stable for at least eight weeks however, in vivo studies were not completed with the stability material to confirm that the complex activity remained the same throughout the stability study.

Materials

Injectable grade polyvinyl pyrrolidone (PVP) (Plasdone C-30, Mw 50 kDa) was from ISP Technologies (Wayne, N.Y.). PVA was from Aldrich (St. Louis, Mo.), Mowiol® PVA was from Gehring-Montgomery, Inc. (Warminster, Pa.), PVA from Spectrum (Gardena, Calif.), Plasmids, containing a CMV promoter and either chloramphenicol acetyltransferase (CMV-CAT) or insulin-like growth factor-I (IGF-I), were prepared and purified at Genemedicine, Inc. Spectra/Por CE (cellulose ester) membranes with a Mw cut-off of 25 kDa were from Spectrum (Houston, Tex.). Sodium Hydroxide NF, Citric Acid Anhydrous Granular USP, and lactose monohydrate were from Penta Manufacturing (Livingston, N.J.). Sterile Water for irrigation, USP (WFI) and 0.9% Sodium Chloride Irrigation, USP were from Baxter Healthcare Corporation (Deerfield, Ill.). Lyophilization vials (10 mL) were from The West Company (Lionville, Pa.). 1% Seakem® Gold Agarose Gel 1× in TAE Buffer for DNA >1 kb were from FMC (Rockland, Me.). The DMED (N,N'-Dimethylethyene-diamine, 99%) solution used was from Aldrich (Milwaukee, Wis.).

Equipment

The following equipment was used to prepare and analyze the formulations and/or components: FISKE ONE-TEN osmometer (Norwood, Mass.), Beckman model DU640 spectrophotometer, Orion model 370 pH meter, FTS Systems™ lyophilizer (Stone Ridge, N.Y.), Molecular Dynamics Fluorimager Model 575, Brookfield DV-III programmable rheometer, and the Vortex Genie 2 from VWR Scientific.

Methods

Preparation of Plasmid/PVP Complexes—Four-vial

This complex was prepared by adding appropriate volumes of WFI, plasmid (lyophilized and re-hydrated to a concentration of ~4 mg/mL), and 25% PVP together and mixing by hand. After waiting for a least 5 minutes, 5 M NaCl was added to the complex, for isotonicity, and again was mixed by hand. The final complex was a four-vial plasmid/PVP (1:17 w/w) complex [3 mg/mL plasmid] in 150 mM NaCl, and each vial contained 1 mL of the complex (FIG. 1).

Preparation of Plasmid/PVP Complexes—Three-vial

This formulation was prepared by preparing a stock solution of 5% PVP and aliquoting the appropriate volume into 10 mL West vials. These vials were lyophilized using an automatic cycle employing a 5% PVP solution of the same volume for the sensor probe. To prepare the final complex, the appropriate volume of plasmid was added to a vial containing the lyophilized PVP. This complex was mixed on a platform vortexer (Vortex Genie 2) at a speed of one (1) until completely re-hydrated. After the complex was completely re-hydrated, an appropriate volume of 1 M NaCl was added to the complex so that the final complex was a three-vial plasmid/PVP (1:17 w/w) complex [3 mg/mL plasmid] in 150 mM NaCl, and each vial contained 1.2 mL of the complex (FIG. 1).

Preparation of Plasmid/PVP Complexes—One-vial

This formulation was prepared by co-lyophilizing plasmid and PVP. A stock solution of plasmid (approx. 5 mg/mL) and a solution of PVP (50 mg/mL) were added together and mixed by hand every five minutes for approximately 30 minutes. This solution was aliquoted into vials so that each vial contained 3.6 mg of plasmid and 60 mg of PVP. These vials were lyophilized using an automatic cycle and a plasmid/PVP formulation of the same volume was used for the sensor control. To prepare the final formulation, 1.1 mL of 0.9% NaCl was added to the lyophilized cake using a 3 cc syringe and a 21 gauge needle and was then mixed on a platform vortexer at a speed of one (1) until completely re-hydrated. The final complex was a one-vial plasmid/PVP (1:17 w/w) complex [3 mg/mL plasmid] in 150 mM NaCl. A volume of 1.1 mL instead of 1.2 mL of the NaCl was added to re-hydrate this complex to compensate for volume exclusion (FIG. 1).

Preparation of Plasmid/PVP Complexes—One-vial pre-neutralized (PN):

This complex was prepared by co-lyophilizing plasmid and PVP (neutralized to pH 7). A stock solution of plasmid (approx. 5 mg/mL) and a solution of PVP (50 mg/mL) pH 7 were added together and mixed by hand every five minutes for approximately 30 minutes. This solution was aliquoted into vials so that each vial contained 3.6 mg of plasmid and 60 mg of PVP (pH 7). These vials were lyophilized using an automatic cycle and a plasmid/PVP complex of the same volume was used for the sensor control. To prepare the final complex, 1.1 mL of 25 mM Na-citrate buffer (pH 4) in 150 mM NaCl was added to the lyophilized cake using a 3 cc syringe and a 21 gauge needle and was then mixed on a platform vortexer at a speed of one (1) until completely re-hydrated. The final complex was a plasmid/PVP (1:17 w/w) complex [3 mg/mL plasmid] in 25 mM Na-citrate buffer (pH 4) in 150 mM NaCl. A volume of 1.1 mL instead of 1.2 mL of the NaCl was added to re-hydrate this complex to compensate for volume exclusion (FIG. 1).

Plasmid/PVP Stability Study

The complexes were prepared as described in Example 1, along with appropriate control solutions. These vials were stored at 4° C., 25° C., and 37° C. and some testing was completed on days 0, 3, 7, 14, 28, and months 4, 6, 8, 10, and 12. Complexes were re-hydrated on the test date and tested for pH, osmolality, percent supercoiled plasmid by gel electrophoresis, composition, in vitro potency, and in vivo potency.

Preparation of Plasmid/PVA Complexes—One-vial Liquid & Frozen Complex (Aldrich and Mowiol®)

This complex was prepared by preparing a stock solution of 15% PVA and aliquoting the appropriate volume into 5 mL West vials so that the final PVA concentration was 3 mg. An appropriate amount of plasmid was added to each of the vials containing PVA so that the plasmid concentration was 3 mg. The plasmid/PVA complexes were mixed by hand until the complex was visually homogenous. An appropriate amount of 5 M NaCl was added to the complexes, so that the final NaCl concentration was 150 mM NaCl, and then mixed by hand. The final complex was a plasmid/PVA (1:10 w/w) complex (3 mg/mL plasmid) in 150 mM NaCl. The "liquid" complexes were immediately stored at 4° C. The "frozen" complexes were immediately flash-frozen in an ethanol/dry-ice bath and then stored at −20° C.

Preparation of Plasmid/PVA Complexes—One-vial Liquid & Frozen Complex (Spectrum)

This complex was prepared by preparing a stock solution of 7.5% PVA and aliquoting the appropriate volume into 5 mL West vials so that the final PVA concentration was 1.5 mg. An appropriate amount of plasmid was added to each of the vials containing PVA so that the plasmid concentration was 3 mg. The plasmid/PVA complexes were mixed by hand until the complex was visually homogenous. After mixing, 30 μL of 5 M NaCl was added to the complexes, so that the final NaCl concentration was 150 mM NaCl, and then mixed by hand. The final complex was a plasmid/PVA (1:5 w/w) complex (3 mg/mL plasmid) in 150 mM NaCl. The "liquid" complexes were immediately stored at 4° C. The "frozen" complexes were immediately flash-frozen in an ethanol/dry-ice bath and then stored at −20° C.

Preparation of Plasmid/PVA Complexes—One-vial Lyophilized Complex (Aldrich & Mowiol®)

This complex was prepared by co-lyophilizing plasmid and PVA. A stock solution of plasmid (approx. 3 mg/mL) and a solution of PVA (150 mg/mL) were added together and mixed by hand every five minutes for approximately 30 minutes. This solution was aliquoted into vials so that each vial contained 3 mg of plasmid and 30 mg of PVA. These vials were lyophilized using an automatic cycle and a plasmid/PVA complex of the same volume was used for the sensor control. The lyophilized complexes were immediately stored at 4° C. until testing. To re-hydrate the complex, 1 mL of 0.9% NaCl was added to the lyophilized cake using a 3 cc syringe and a 21 gauge needle and was then mixed on a platform vortexer at a speed of one (1) until completely re-hydrated. The final complex was a plasmid/PVA (1:10 w/w) complex (3 mg/mL plasmid) in 150 mM NaCl.

Preparation of Plasmid/PVA Complexes—One-vial Lyophilized Complex (Spectrum)

This complex was prepared by co-lyophilizing plasmid and PVA. A stock solution of plasmid (approx. 3 mg/mL) and a solution of PVA (7.5 mg/mL) were added together and mixed by hand every five minutes for approximately 30 minutes. This solution was aliquoted into vials so that each vial contained 3 mg of plasmid and 15 mg of PVA. These vials were lyophilized using an automatic cycle and a plasmid/PVA complex of the same volume was used for the sensor control. The lyophilized complexes were immediately stored at 4° C. until testing. To re-hydrate the complex, 1 mL of 0.9% NaCl was added to the lyophilized cake using a 3 cc syringe and a 21 gauge needle and was then mixed on a platform vortexer at a speed of one (1) until completely re-hydrated. The final complex was a plasmid/PVA (1:5 w/w) complex (3 mg/mL plasmid) in 150 mM NaCl Plasmid/PVA Stability Study The complexes were prepared as described above along with appropriate control solutions. The frozen complexes were stored at −20° C. until tested, and the liquid and lyophilized complexes were stored at 4° C. until tested. The plasmid/PVA complexes were tested on day 0, week 1, 2, 4, 6, and 8. The complexes were tested for pH, osmolality, percent supercoiled plasmid by gel electrophoresis, composition, and viscosity. The lyophilized complexes were re-hydrated on the day of testing.

Preparation of PVP Stock Solutions

Stock solutions of polymers were made by dissolving the polymers in WFI on a weight/volume (% w/v) basis. The 5% PVP (PN) was prepared by adding an appropriate volume of 5 M NaOH to the stock before the solution had been q.s. so that the final pH was 7. The 25% PVP stock solution was sterilized by autoclaving at 120 minutes for 20 minutes. The 5% PVP and 5% PVP (PN) was sterilized by filtering through a 0.2 μm Nalgene filter unit.

Preparation of PVA Stock Solutions

PVA stock solutions were made by dissolving the polymer in WFI on a weight/volume (% w/v) basis. The solutions were heated while mixing on a stir-plate until dissolved; then the solutions were cooled to room temperature and then q.s. to fill line. All PVA stock solutions were sterilized by filtering through a 0.2 μm Nalgene filter unit.

Preparation of 25 mM Sodium-citrate Buffer (pH 4) in 150 mM NaCl

This solution was prepared by dissolving 100 mL of citric acid anhydrous in 0.9% NaCl on a weight/volume (% w/v) basis so that the final concentration was 50 mM citric acid in 150 mM NaCl. Another solution of NaOH was prepared by dissolving 100 mL of NaOH in 0.9% NaCl on a weight/volume (% w/v) basis so that the final concentration was 50 mM NaOH in 150 mM NaCl. These solutions were added together so that the final solution was 25 mM sodium-citrate buffer in 150 mM NaCl. Next, a small amount of 5 M NaOH was added to the buffer so that the final pH was 7. This solution was sterilized by filtering through a 0.2 μm Nalgene filter unit.

Preparation of 25% Lactose Solution

The stock solutions of lactose were made by dissolving the lactose in WFI on a weight/volume (% w/v) basis. The 25% lactose was sterilized by filtering through a 0.2 μm Nalgene filter unit.

In vivo Studies in Muscle

Formulations were administered to five to six week old male rats (Fischer 344 strain, 120–130 grams) from Harlan Sprague Dawley Laboratories. A 2–4 mm incision in the skin was make aseptically in anesthetized rats and 50 μL of the formulation was injected into the tibalis muscle of both legs using a 28-gauge needle. Rats were sacrificed at 7 days post-administration, the tibialis muscles were harvested and muscle extracts were prepared. The levels of CAT expression were determined according to the CAT ELISA calorimetric enzyme immunoassay from Boehringer-Mannheim (Mannheim, Germany). The CAT expression was normalized to total muscle protein in the sample, which was measured using a Coomassie Blue G250-based assay (Bio-Rad; Hercules, Calif.). NIH guidelines for the care and use of laboratory animals were observed. CAT in skeletal muscle extracts was quantitated using a commercially available ELISA kit from Boehringer Mannheim.

In vivo Studies in Solid Tumor

Complexes were administered to 8–10 week old female mice (C3H strain, 20–25 gm) from Charles River Laboratories bearing two SCCVII tumors (averaging ~35 mm$^3$) subcutaneously on the left and right super-inguinal area of the flank. To create the model, the implantation site was shaved and SCCVII cells (4E5/30 μL) were implanted subcutaneously using a 28-gauge needle in each area (right and left flank). The tumors are allowed to grow to five days post-implantation to reach the previously mentioned size. On day five post-implantation, the animals were sedated with 2.5 mg/kg Acepromazine intra-peritoneally. Once sedated, the tumors were swabbed with 70% isopropyl alcohol and were injected with 50 μL of the complex using a 28-gauge needle. The mice were humanely euthanized at 24 hours post-injection; the tumors were harvested and stored in tubes with beads and placed into liquid nitrogen. NIH guidelines for the care and use of laboratory animals was used. The tumors were homogenized by bead beating and the supernatant was assayed for CAT expression.

In vitro Studies

Transfection efficiency of the plasmid/PVP (1:17 w/w) complexes [3 mg/mL plasmid] in 150 mM NaCl was studied in mouse myoblasts cell line, $C_2C_{12}$. These cells were grown in Dulbecco's Modified Eagle Medium (DMEM) media supplemented with 10% Fetal Bovine Serum. The transfections were performed in six well plates at 60–80% cell density with 5 μg of plasmid and 30 μg of Lipofectamine™ per well. Culture medium was removed and replaced with DMEM containing 2% horse serum for the initiation of myotube differention process 16 hours after the initial transfection. The supernatants of the cells were harvested 96 hours later for IGF-I analysis.

Gel Electrophoresis

The plasmid concentration was determined by $A_{260}$, and the samples were diluted to 100 μg/mL in 20 mM Tris HCl. 3 μL of these samples was aliquoted into 0.5 mL tubes with 7 μL of 1× loading dye. The samples with dye were loaded onto a 1% FMC Reliant® gel. The gels were run for approximately 1 hour at 100 volts. The gels were stained with SYBR® Green II for approximately 20 minutes and de-stained in distilled water for approximately 30 minutes. The gels were scanned on the fluorimager analyzed using Image Quan™ software:

Abasic Damage by Gel Electrophoresis 100 mM DMED solution was prepared by adding 2.5 mL of WFI, 26.6 μL of DMED solution, 20 μL of concentrated acetic acid. The final pH was between 7.3 and 7.4. The test samples were diluted to 100 μg/mL in 20 mM Tris-HCl, pH 7.5. Samples were prepared from the previous dilution by adding 1 μL of the sample to 19 μL of 20 mM Tris; this is the control sample. The test sample was prepared by adding 1 μL of sample to 19 μL of DMED solution. These reactions were incubated at 37° C. for 30 minutes. Then, 2 μL of 10×loading dye was added to the samples. 5 μL of the samples were loaded onto a 0.4% gel. The gel was stained in SYBR® Green II and then scanned on the fluorimager where the plasmid bands were quantitated. The following equation was used to determine the abasic sites per molecule of plasmid Abasic sites per plasmid=Ln % SC plasmid/% SC plasmid [treated with DMED]

Viscosity

Viscosity of the plasmid/PVA complexes was measured using a Brookfield model DV-III viscometer. A viscosity standard was measured before each series of sample measurements. The viscosity of each complex was measured only once due to the sample size necessary for this test. The viscosity results are recorded in CentiPoise (cP).

EXAMPLE 1

Plasmid/PVP Examples pH

For the formulations stored at 4° C., the four vial formulation maintained its pH of approximately 4, which has been determined to be optimal for in vivo potency. The three-vial formulation, after re-hydration, had an average pH value of approximately 4.3 with individual pH values varying up to 0.3 pH units. The one-vial formulation, after re-hydration, showed an average pH of 4.1, with a variance of 0.3 pH units. The one-vial (PN) formulation, which was re-hydrated with sodium-citrate buffer (pH 4.0), showed no change from the pH of the buffer. There appeared to be no effect of storage temperature on pH values.

Osmolality

Of the 4° C. stored formulations, both the four-vial and three-vial formulations were more hypertonic than the one-vial formulation, which showed only moderate hypertonicity. The three-vial formulation is more hypertonic because 200 μL of 1 M NaCl is added to the complex with a final volume of 1.1 mL. This makes the final NaCl concentration 181.8 mM whereas the four-vial, one-vial, and one-vial (PN) are made with a final concentration of 150 mM NaCl. The one-vial (PN) formulation was slightly hypotonic, with an average value of 270 mOsm. The storage conditions had no apparent effect on the osmolality of the formulations.

Supercoiled Plasmid by Gel Electrophoresis

Four-vial: The effect of storage temperature had a significant effect on the amount of supercoiled plasmid in the four-vial formulation. After only three days, there was no remaining supercoiled plasmid in the formulation stored at 37° C. For formulations stored at 25° C., 50% of the supercoiled form was lost by day 3, and no remaining supercoiled was evident by month four. The formulations stored at 4° C. maintained their supercoiled up to two weeks with a significant drop-off by one month. By six months, less than 10% supercoiled plasmid remained in the four-vial formulation. This lack of stability is most likely due to the fact that the plasmid has been lyophilized in the absence of a cryoprotectant.

Three-vial: The three-vial formulation maintained its supercoiled plasmid at all three storage conditions up to 1 month. After 1 month the 37° C. stored material had no remaining SC plasmid, and the 25° C. material began to lose its SC until month 12 where the SC plasmid is no longer evident. The 4° C. material maintained its SC plasmid throughout the course of testing.

One-vial: The formulations stored at 37° C. lost all of its supercoiled plasmid by day 13, and the formulations stored at 25° C. showed no remaining SC plasmid by four months. The SC plasmid for the one-vial formulation was maintained only for the material stored at 4° C. showing a slight (20% loss) over twelve months.

One-vial (PN): For the one-vial (PN) formulation, the data appear very similar to the one-vial formulation with the 37° C. stored material having some SC plasmid up to one month. Again the 4° C. stored material maintained most of its SC plasmid for the entire 12 months.

Comparing the supercoiled plasmid of the four-vial, three-vial, one-vial, and one-vial (PN) over time at 40° C. shows that the three-vial and the one-vial (PN), which retain most of their supercoiled form, are more stable than the one-vial and the four-vial. The four-vial formulation has less than 10% supercoiled form at six months.

Comparing the one-vial (PN) formulation to lyophilized plasmid at 4° C. demonstrates that the one-vial (PN) formulation protects the plasmid from degradation in terms of supercoiled form. The one-vial (PN) formulation has some loss of supercoiled form over time, 41% over 12 months whereas the lyophilized plasmid has a much greater loss of supercoiled form over time, 75% loss after four months and 100% loss after 12 months of storage. The plasmid was also stored at 25° C. to demonstrate accelerated stability of the plasmids. The data is essentially the same as the 4° C. data; both plasmids stored in water are more stable than the lyophilized plasmid A comparison of the percent supercoiled plasmid of plasmid stored in water at two different concentrations and lyophilized plasmid stored over time at 4° C. shows that both of the liquid plasmids are very stable over time and retain most of their supercoiled form, but the lyophilized plasmid began to lose its supercoiled form after one week and by one month it had lost 90–100% of its supercoiled form.

A comparison was also made of supercoiled plasmid of the plasmid in water, lyophilized plasmid, and the one-vial (PN) formulation. This data shows that the plasmid stored in an aqueous solution is much more stable than the lyophilized plasmid and that the one-vial (PN) formulation protects the plasmid during the lyophilization process from the same degradation that is incurred by the plasmid lyophilized alone.

Abasic Sites per Plasmid Molecule by Gel Electrophoresis

An assay was completed for only one month of the stability study and showed the abasic damage for the aqueous plasmid, lyophilized plasmid, and the four different plasmid/PVP (1:17 w/w) formulations. There is no real numeric value that can be given as a limit for abasic damage therefore the values given must be compared to each other.

In vitro Potency

The expression of IGF-I after in vitro transfection of $C_2C_{12}$ cells with the four formulations after storage at 4° C. showed a certain amount of variation in the assay, but there appeared to be no difference in transfection efficiency between any of the four formulations.

In vivo Potency

No significant difference in expression of CMV-CAT in mouse gastrocnemius muscle after i.m. administration of the 4° C. stored stability formulations was evident between any of the four formulations up to one month. At the next time-point tested, 6 months, only the one-vial (PN) and the three-vial formulations showed any expression and this was comparable to the expression seen at day 0.

The animals injected with the pH 3.0–4.0 formulations gave 4-fold higher β-gal expression levels of a plasmid/5% PVP formulation in vivo than the animals injected with the pH of 5.5–6.0 and 7.0–7.5.

Example 2

Plasmid/PVA Results pH Results

The pH results of the different plasmid/PVP complexes are quite different from each other. The pH of the liquid, frozen, and lyophilized Aldrich complexes are approximately 5.0 and are very similar to each other. The Mowiol® complexes are different in that the liquid and frozen complexes are approximately 5.5, whereas the pH of the lyophilized complexes is about 5.0. The pH of the Spectrum PVA complexes also differs from the others in that the pH of the liquid and frozen complexes are between 5.5 and 6.0, but the lyophilized complexes are between 4.25 and 4.5. This is the greatest difference between storage conditions. The Spectrum PVA is advantageous over the other manufacturers since the liquid and frozen pH is higher, and the plasmid will be more stable at this pH.

Osmolality Results

The osmolality of the plasmid/PVA complexes is unremarkable. The osmolality of the Aldrich complexes was approximately 320 mOsm, the Mowiol® complexes were also approximately 320 mOsm, and the Spectrum complexes averaged approximately 310 mOsm.

Gel Electrophoresis Results

The gel electrophoresis results of the different plasmid/PVA complexes are very similar to each other. The Aldrich, Mowiol®, and Spectrum liquid and frozen complexes were all between 60–80% supercoiled plasmid. The lyophilized complexes for each of the manufacturers was significantly lower that the liquid and frozen complexes, between 40–60% supercoiled plasmid, indicating that the lyophilized complexes are less stable than the liquid and frozen complexes.

Abasic Sites Per Plasmid Molecule by Gel Electrophoresis

There is no trend evident for abasic damage of the plasmid/PVA complexes.

Viscosity Results

The viscosities of the Aldrich and Mowiol® liquid and frozen complexes were approximately 7–8 cP and are similar to each other. The viscosity of the Aldrich and Mowiol® lyophilized complexes were very inconsistent ranging from 5.5–11 cP at different time points. The viscosity of the Spectrum complexes are similar to the other materials since the lyophilized complexes are also inconsistent for each time point ranging from 8–14 cP. However, the viscosity of the Spectrum material is intrinsically higher than the Aldrich and Mowiol® material so the liquid and frozen complexes average approximately 9 cP. The lyophilized complexes were difficult to lyophilize and even after four hours of re-hydration time some solid could be seen in the vials. The inconsistent viscosity measurements are most likely due to the difficulty in re-hydration.

In Vivo Results

These data show that the plasmid/PVA complex (1:10 w/w) gives approximately twice the levels of CAT expression in the tumor than plasmid alone at the same dose.

one skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A co-lyophilized complex comprising:
   a nucleic acid vector;
   a formulating agent;
   one or more anti-oxidants; and
   wherein a solution comprising the nucleic acid vector and a solution comprising the formulating agent are admixed to form a lyophilization solution prior to co-lyophilization and wherein the formulating agent protects the nucleic acid vector from freezing degradation.

2. An in-line mixer containing a liquid, wherein said in-line mixer comprises a confined flowing system and said liquid comprises isolated, enriched or purified nucleic acid molecules; and
   wherein said in-line mixer contains one or more other liquids, wherein at least one of said other liquids comprises one or more formulating agents selected from the group consisting of a lipid, a peptide, and a polymer.

3. The mixer of claim 2, wherein said formulating agent is a protective, interactive, non-condensing compound.

4. The mixer of claim 3, wherein said formulating agent is polyvinyl pyrrolidone.

5. The mixer of claim 3, wherein said formulating agent is polyvinyl alcohol.

6. The mixer of claim 2, wherein said formulating agent protects said nucleic acid against freezing and increases transfection rates.

7. The mixer of claim 2, wherein said formulating agent is selected from the group consisting of: one or more polyvinyl pyrrolidones, one or more cationic lipids, one or more cationic lipids with neutral co-lipids, one or more liposomes, one or more peptides, and one or more lipopeptides.

8. A method of using an in-line mixer containing a liquid comprising isolated, enriched or purified nucleic acid molecules, said method comprising:
   the step of combining said liquid comprising isolated, enriched or purified nucleic acid molecules with one or more other liquids in said in-line mixer;
   wherein said liquids are continuously mixed;
   wherein the liquids are combined at a Reynolds number of at least 373; and
   wherein said in-line mixer comprises a confined flowing system.

9. The method of claim 8, wherein the liquids are combined at a Reynolds number of at least 560.

10. The method of claim 9, wherein the liquids are combined at a Reynolds number of at least 746.

11. A method of using an in-line mixer containing a liquid comprising isolated, enriched or purified nucleic acid molecules, said method comprising:
    the step of combining said liquid comprising isolated, enriched or purified nucleic acid molecules with one or more other liquids in said in-line mixer;
    wherein said liquids are continuously mixed;
    wherein said homogenous mixture comprises particles with diameters of about 100 nanometers or less; and
    wherein said in-line mixer comprises a confined flowing system.

12. The method of claim 11, wherein said homogenous mixture comprises particles with diameters of about 75 nanometers or less.

13. The method of claim 12, wherein said homogenous mixture comprises particles with diameters of about 50 nanometers or less.

14. A co-lyophilized complex comprising a nucleic acid molecule in a vector and a formulating agent that protects said nucleic acid molecule against freezing and increases transfection rates; and wherein said formulating agent is pre-neutralized polyvinyl-pyrrolidone.

15. The complex of claim 14, wherein said protective interactive non-condensing compound is polyvinyl pyrrolidone present in a concentration of at least 2.5%. pyrrolidone.

16. The complex of claim 14, wherein said protective interactive non-condensing compound is polyvinyl pyrrolidone with a molecular weight of at least 80 kDa.

17. A co-lyophilized complex comprising a nucleic acid molecule in a vector and a formulating agent that protects said nucleic acid molecule against freezing and increases transfection rates; and wherein said formulating agent is polyvinyl alcohol.

18. A co-lyophilized complex comprising:
    a nucleic acid molecule in a vector;
    a formulating agent that protects said nucleic acid molecule against freezing and increases transfection rates; and
    one or more antimicrobial agents.

19. The complex of claim 18, wherein said antimicrobial agents are independently selected from the group consisting of Benzalkonium chloride, Benzyl alcohol, Chlorocresol, Phenylmercuric nitrate, and acetate.

20. A co-lyophilized complex comprising:
    a nucleic acid molecule in a vector;
    a formulating agent that protects said nucleic acid molecule against freezing and increases transfection rates; and
    one or more anti-oxidants.

21. The complex of claim 20, wherein said anti-oxidants are independently selected from the group consisting of Ascorbic acid, Butylhydroxyanisole (BHA), Cysteine, Sodium bisulfate, and Glutathione.

22. A co-lyophilized complex comprising:
    a nucleic acid molecule in a vector;
    a formulating agent that protects said nucleic acid molecule against freezing and increases transfection rates; and
    one or more buffers independently selected from the group consisting of Acetic acid and salt, Succinic acid and borax, Formate and HCl, and Na-citrate buffer.

23. A method of making a co-lyophilized complex comprising a nucleic acid molecule in a vector and a formulating agent that protects said nucleic acid molecule against freezing and increases transfection rates, said method comprising the step of combining a first liquid comprising said nucleic acid molecule in a vector and a second liquid comprising said formulating agent in an inline mixer.

24. The method of claim 23, wherein said liquids are continuously mixed.

25. The method of claim 23, wherein the liquids are combined at a Reynolds number of at least 373.

26. The method of claim 25, wherein the liquids are combined at a Reynolds number of at least 560.

27. The method of claim 26, wherein the liquids are combined at a Reynolds number of at least 746.

28. The method of claim 23, wherein said liquids are combined under conditions which produce a homogenous mixture.

29. The method of claim 23, wherein said homogenous mixture comprises particles with diameters of about 100 nanometer or less.

30. The method of claim 29, wherein said homogenous mixture comprises particles with diameters of about 75 nanometers or less.

31. The method of claim 30, wherein said homogenous mixture comprises particles with diameters of about 50 nanometers or less.

32. The method of claim 23, wherein said liquids are combined with one other liquid.

33. The method of claim 23, wherein said liquids are combined with two or more other liquids.

34. A method of making a nucleic acid formulation for gene transfer comprising the step of combining a nucleic acid solution with a formulating agent solution to form a homogenous mixture using a continuous flow in-line mixer.

35. A co-lyophilized complex comprising a nucleic acid vector and a formulating agent, wherein a solution comprising the nucleic acid vector and a solution comprising the formulating agent are admixed to form a lyophilization solution prior to co-lyophilization and wherein the formulating agent protects the nucleic acid vector from freezing degradation, wherein the formulating agent comprises a non-condensing amphiphilic polymer selected from the group consisting of polyvinyl-pyrrolidone, polyvinyl alcohol, poloxamers, and poloxamines.

36. The co-lyophilized complex of claim 35, wherein said nucleic acid vector and said polymer are admixed in said lyophilization solution at a ratio between about 1:1 and about 1:30 weight to weight.

37. The co-lyophilized complex of claim 35, wherein said formulating agent comprising polyvinyl-pyrrolidone is pre-neutralized prior to admixing with the nucleic acid.

38. The co-lyophilized complex of claim 37, wherein said lyophilization solution has a pH of about 3.5 to about 9.

39. A co-lyophilized complex comprising:

a nucleic acid vector;

a formulating agent;

one or more antimicrobial agents; and wherein a solution comprising the nucleic acid vector and a solution comprising the agent are admixed to form a lyophilization solution prior to co-lyophilization and formulating agent protects the nucleic acid vector from freezing degradation.

* * * * *